(12) United States Patent
Ihara et al.

(10) Patent No.: US 10,016,409 B2
(45) Date of Patent: *Jul. 10, 2018

(54) METHOD FOR IMPROVING INTERSTITIAL FLOW

(71) Applicant: FOUNDATION FOR BIOMEDICAL RESEARCH AND INNOVATION, Hyogo (JP)

(72) Inventors: Masafumi Ihara, Hyogo (JP); Takakuni Maki, Hyogo (JP); Akihiko Taguchi, Hyogo (JP)

(73) Assignee: FOUNDATION FOR BIOMEDICAL RESEARCH AND INNOVATION AT KOBE, Kobe-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/650,554

(22) Filed: Jul. 14, 2017

(65) Prior Publication Data
US 2017/0312265 A1 Nov. 2, 2017

Related U.S. Application Data

(63) Continuation of application No. 14/860,057, filed on Sep. 21, 2015, now Pat. No. 9,737,524, which is a continuation of application No. 14/407,692, filed as application No. PCT/JP2013/003740 on Jun. 14, 2013, now abandoned.

(30) Foreign Application Priority Data

Jun. 15, 2012 (JP) .................................. 2012-135906
Oct. 5, 2012 (JP) .................................. 2012-223580

(51) Int. Cl.
| | | |
|---|---|---|
| *A61K 31/47* | (2006.01) | |
| *A61K 31/4709* | (2006.01) | |
| *C07D 401/12* | (2006.01) | |
| *A61K 9/00* | (2006.01) | |
| *A61K 9/14* | (2006.01) | |

(52) U.S. Cl.
CPC ........ *A61K 31/4709* (2013.01); *A61K 9/0019* (2013.01); *A61K 9/14* (2013.01); *C07D 401/12* (2013.01)

(58) Field of Classification Search
CPC .................................................. C07D 401/04
USPC ....................................................... 514/312
See application file for complete search history.

(56) References Cited

U.S. PATENT DOCUMENTS

| | | | |
|---|---|---|---|
| 6,228,398 B1 | 5/2001 | Devane et al. | |
| 9,737,524 B2 * | 8/2017 | Ihara ................... | A61K 31/4709 |
| 2002/0054907 A1 | 5/2002 | Devane et al. | |
| 2003/0129237 A1 | 7/2003 | Devane et al. | |
| 2003/0170304 A1 | 9/2003 | Devane et al. | |
| 2004/0197405 A1 | 10/2004 | Devane et al. | |
| 2006/0154963 A1 | 7/2006 | Hong | |
| 2006/0240105 A1 | 10/2006 | Devane et al. | |
| 2007/0122481 A1 | 5/2007 | Liversidge et al. | |
| 2007/0160675 A1 | 7/2007 | Devane et al. | |
| 2008/0102121 A1 | 5/2008 | Devane et al. | |
| 2008/0113025 A1 | 5/2008 | Devane et al. | |
| 2008/0118556 A1 | 5/2008 | Devane et al. | |
| 2008/0279929 A1 | 11/2008 | Devane et al. | |
| 2009/0149479 A1 | 6/2009 | Jenkins et al. | |
| 2009/0297596 A1 | 12/2009 | Devane et al. | |
| 2009/0297597 A1 | 12/2009 | Liversidge et al. | |
| 2009/0297602 A1 | 12/2009 | Devane et al. | |
| 2010/0113515 A1 | 5/2010 | Hong | |
| 2010/0136106 A1 | 6/2010 | Liversidge et al. | |
| 2010/0247636 A1 | 9/2010 | Devane et al. | |
| 2010/0292281 A1 | 11/2010 | Lovell et al. | |
| 2010/0298375 A1 | 11/2010 | Arai | |
| 2011/0008435 A1 | 1/2011 | Devane et al. | |
| 2011/0064803 A1 | 3/2011 | Devane et al. | |
| 2013/0053350 A1 | 2/2013 | Colca et al. | |
| 2013/0065921 A1 | 3/2013 | Hong | |

FOREIGN PATENT DOCUMENTS

| | | |
|---|---|---|
| JP | 2006-518732 | 8/2006 |
| JP | 2008-545808 | 12/2008 |
| JP | 4590397 | 12/2010 |
| WO | WO 2004/075897 A1 | 9/2004 |
| WO | WO 2008/030209 A2 | 3/2008 |
| WO | WO 2008/143361 A1 | 11/2008 |
| WO | WO 2011/075514 A1 | 6/2011 |

OTHER PUBLICATIONS

International Search Report from the Japanese Patent Office for International Application No. PCT/IB2013/003740, dated Jul. 16, 2013.
Saito et al.; "Neuropathology of Mild Cognitive Impairment", Symposium: Brain Imaging and Neuropathology, Neuropathology, vol. 27, pp. 578-584, (2007).
Yamamoto; "Current Topics about Mild Cognitive Impairment (MCI)", Psychiatria et Neurologia Japonica, vol. 113, No. 6, pp. 584-592, (2011).

(Continued)

*Primary Examiner* — Raymond J Henley, III
(74) *Attorney, Agent, or Firm* — Oblon, McClelland, Maier & Neustadt, L.L.P.

(57) ABSTRACT

Provided is a prophylactic and/or therapeutic drug for mild cognitive impairment, which can improve interstitial flow in cerebral blood vessel and the like to achieve sufficient clearance of harmful proteins accumulated in the brain. The prophylactic and/or therapeutic drug includes 6-[4-(1-cyclohexyl-1H-tetrazole-5-yl)butoxy]3,4-dihydrocarbostyril or a salt thereof as an active ingredient. The prophylactic and/or therapeutic drug can improve a flow of interstitial fluid around blood vessels in a drainage pathway to excrete harmful proteins. The prophylactic and/or therapeutic drug for mild cognitive impairment may take the form of a pharmaceutical product for oral administration, a liquid pharmaceutical product for oral administration, or an injectable preparation. The prophylactic and/or therapeutic drug for mild cognitive impairment can be used for the prevention and/or treatment of cerebral amyloid angiopathy, and can also be used for improvement of Lewy body disease, Down's syndrome, or macular degeneration.

4 Claims, 17 Drawing Sheets

(56) References Cited

OTHER PUBLICATIONS

Peterson et al.; "Vitamin E and Donepezil for the Treatment of Mild Cognitive Impairment", The New England Journal of Medicine, vol. 352, No. 23, pp. 2379-2388, (2005).
Gresele et al.; "Anti-Platelet Therapy: Phosphodiesterase Inhibitors", BJCP British Journal of Clinical Pharmacology, vol. 72, No. 4, pp. 634-646, (2011).
Kasahara et al.; "Cilostazol Reduces the Risk of Hemorrhagic Infarction After Administration of Tissue-Type Plasminogen Activator in a Murine Stroke Model", Stroke, vol. 43, pp. 499-506, (2012).
Tanaka et al.; "Effects of a Selective Inhibitor of Cyclic AMP Phosphodiesterase on the Pial Microcirculation in Feline Cerebral Ischemia", Phosphodiesterase Inhibitor, Stroke, vol. 20, pp. 668-673, (1989).
Park et al.; "Protective Effect of the Phosphodiesterase III Inhibitor Cilostazol on Amyloid β-Induced Cognitive Deficits Associated with Decreased Amyloid β Accumulation", Biochemical and Biophysical Research Communications, vol. 408, pp. 602-606, (2011).
Kamiyama et al.; "Potential Hippocampal Region Atrophy in Diabetes Mellitus Type 2: A Voxel-Based Morphometry VSRAD Study", Japan Journal of Radiol., vol. 28, pp. 266-272, (2010).
Hiramatsu et al.; "Cilostazol Prevents Amyloid β Peptide$_{25-35}$ Induced Memory Impairment and Oxidative Stress in Mice", British Journal of Pharmacology, vol. 161, pp. 1899-1912 (2010).
Sakurai et al.; "Effects of Cilostazol on Cognition and Regional Cerebral Blood Flow in Patients with Alzheimer's Disease and Cerebrovascular Disease: A Pilot Study", Geriatr Gerontol Int., vol. 13, pp. 90-97, (2013).
LETTER; "A Combination Therapy of Donepezil and Cilostazol for Patients with Moderate Alzheimer Disease: Pilot Follow-Up Study", Am J Geriatr Psychiatry, vol. 17, No. 4, pp. 353-354, (2009).
Johnson; "Late-Onset Neurodegenerative Diseases—the Role of Protein Insolubility", J. Anat., vol. 196, pp. 609-616, (2000).
Ishii; "Current Status of Amyloid PET in Pathophysiological Research and Drug Development for Alzheimer's Disease", Proceedings of Annual Meeting of the Japanese Research Group on Senile Dementia, vol. 18, pp. 84-88, (2011).
Weller et al.; "Lymphatic Drainage of the Brain and the Pathophysiology of Neurological Disease", Acta Neuropathol, vol. 117, No. 1, pp. 1-14, (2009).
Okada et al.; "A Combined Therapy of Cilostazol and Donepezil Hydrochloride for Sufferers of Both Ischemic Cerebrovascular Disease and Mild Cognitive Impairment", 35$^{th}$. The Japan Stroke Society News Part3, 14 pages, (2010).
Marsh et al.; "Examining the Mechanisms that Link β-Amyloid and α-Synuclein Pathologies", Alzheimer's Research & Therapy, 4:11, pp. 1-8 (2012).
Staekenborg et al.; Progression of Mild Cognitive Impairment to Dementia Contribution of Cerebrovascular Disease Compared With Medial Temporal Lobe Atrophy, Stroke, pp. 1269-1274, (2009).
Boeve; "Mild Cognitive Impairment Associated with Underlying Alzheimer's Disease Versus Lewy Body Disease", Parkinsonism and Related Disorders, 1851, pp. S41-S44, (2012).
Schley et al.; Mechanisms to Explain the Reverse Perivascular Transport of Solutes out of the Brain, Journal of Theoretical Biology, 238, pp. 962-974, (2006).
Hawkes et al.; "Perivascular Drainage of Solutes is Impaired in the Ageing Mouse Brain and in the Presence of Cerebral Amyloid Angiopathy", Acta Neuropathol, 121, pp. 431-443, (2011).
Shinohara et al.; Cilostazol for Prevention of Secondary Stroke (CSPS 2): an Aspirin-Controlled, Double-Blind, Randomised Non-Inferiority Trial, Articles, Lancet Neurol, vol. 9, 959-968, (2010).
Daijiten; "Lymphatic Circulation" Nanzando's Medical Dictionary, 17th Edition, 1990, pp. 2054-2055 (w/ partial English translation)
Notice of Reasons for Rejections dated Oct. 21, 2014, in Japanese Patent Application No. 2014-520940 filed Jun. 14, 2013 (with partial English translation).
Iwabuchi, et al., "Effects of Administering Cilostazol to Patients with Mild Dementia—Cognition Function and Change in Cerebral Blood Flow", Stroke, vol. 30, No. 2, p. 328 (2008) (with partial English translation).
Imafuku, et al., "Effects of Treating Cerebrovascular Dementia Using Cilostazol", Stroke, vol. 30, No. 2, p. 330 (2008) (with partial English translation).
Murayama, et al., "Neuropathology of Mild Cognitive Impairment", Advances in Neurological Sciences, vol. 48, No. 3, pp. 441-449 (2004) (with partial English translation).
Celsis (2000). "Age-related cognitive decline, mild cognitive impairment or preclinical Alzheimer's disease." Annals of Medicine, 32(1):6-14.
Yamamoto, "Recent Issues on Mild Cognitive Impairment (MCI)", Psychiatria et Neurologia Japonica, vol. 113, No. 6, pp. 584-592 (2011) (with partial English translation).
Akihiko Taguchi, et al. "Cilostazol improves cognitive function in patients with mild cognitive impairment: a retrospective analysis", Psychogeriatrics, vol. 13, No. 3, XP055216951, 2013, pp. 164-169.

* cited by examiner

METHOD FOR IMPROVING INTERSTITIAL FLOW

CROSS REFERENCE TO RELATED APPLICATIONS

The present application is a continuation of U.S. patent application Ser. No. 14/860,057 (now U.S. Pat. No. 9,737,524), filed on Sep. 21, 2015, which is a continuation of U.S. patent application Ser. No. 14/407,692 (abandoned), filed on Dec. 12, 2014, which is a 35 U.S.C. § 371 national stage patent application of international patent application PCT/JP2013/003740, filed on Jun. 14, 2013, which claims priority to Japanese patent applications: JP 2012-223580, filed Oct. 5, 2012; and JP 2012-135906, filed on Jun. 15, 2012.

TECHNICAL FIELD

The present invention relates to a prophylactic and/or therapeutic agent for mild cognitive impairment that can improve the function of cranial nerves by enhancing the function of brain interstitial flow as a drainage pathway of harmful proteins in a central nervous system.

BACKGROUND ART

Mild cognitive impairment (MCI) is a syndrome of cognitive impairment that is not significant enough to interfere with daily activities unlike dementia and does not hinder basic dairy life, but causes a memory loss of an important promise and difficulty in travelling to a first place, for example.

In an initial stage of MCI, mild impairment of cognitive function is observed irrespective of the type of accumulated harmful proteins, but irreversible alteration of cranial nerve tissues has not occurred yet in many cases. On the other hand, in patients already suffering from dementia, such as dementia caused by cerebral amyloid angiopathy, frontotemporal dementia, Lewy body dementia, Alzheimer-type dementia, and dementia caused by Parkinson's disease, pathologically irreversible neurodegeneration is often observed.

MCI is not merely a previous stage of specific dementia, such as dementia caused by cerebral amyloid angiopathy, frontotemporal dementia, Lewy body dementia, Alzheimer-type dementia, cerebrovascular dementia, dementia caused by Parkinson's disease, and prion disease. In MCI patients, various pathological changes such as Lewy body change, progressive supranuclear palsy change, Alzheimer change, argyrophilic grain change, vascular disorder change are observed, and these changes are opposite to a single pathological change (see Non-patent Document 1).

As described above, MCI should be distinguished from various known types of dementia, and is actually considered as such. In a "Guidelines for Management of Dementia" (http://www.neurology-jp.org/guidelinem/nintisyo.html) published on the homepage of Japanese Society of Neurology, MCI is listed in parallel with general dementia, and is treated as a disease distinguished from dementia. To make a diagnosis of MCI, "the presence of a difficulty in daily activities", "a decreased cognitive function", and "the absence of a diagnosis of dementia" are checked, and then, the case is classified as amnestic MCI or non-amnestic MCI depending on the presence or absence of memory impairment, and is further segmented (see the guideline, chapter 4: Progress and Therapeutic Strategy, B. mild cognitive impairment, item CQ IV B-1, pp. 108-109).

An MCI patient may be able to remain in an MCI state, or may be converted to one of the above-mentioned types of dementia. Thus, even if a drug is statistically demonstrated to be effective for a specific dementia such as Alzheimer-type dementia, cerebrovascular dementia, Lewy body-type dementia, frontotemporal dementia, or dementia caused by Parkinson's disease, it is still unknown that the drug is effective for MCI. For this reason, if a diagnosis of MCI is made, since MCI can be converted to various types of dementia as described above, it is apparent that risk manage and MCI treatment at an early stage are preferable especially for elderly people of 65 years of age or more.

Many clinical trials have been actually conducted on known dementia therapeutic drugs in order to confirm an effect on MCI. However, the "Guidelines for Management of Dementia" above shows a result that an effectiveness on MCI patients is very limited or is not present with respect to donepezil (Aricept), rivastigmine (Exelon), and galantamine (Reminyl), which are well-known dementiatherapeutic drugs as acetylcholinesterase inhibitors. From this result, it is concluded that these drugs have no prophylactic effects of conversion from MCI to dementia or Alzheimer (see the guideline, chapter 4: Progress and Therapeutic Strategy, p. 115). This is also shown in Non-patent Document 2 (see especially item 3, p. 585).

The guideline also shows that in a randomized controlled trial (RCT) directed to postmenopausal women of 65 years of age or more without dementia, estrogen unexpectedly increased the risk of onset of dementia or MCI significantly (see the guideline, pp. 115-116, Item 2. Other Drugs (1)), and even administration of rofecoxib (an COX-2 inhibitor) of a nonsteroidal anti-inflammatory drug showed no prophylactic effects (see the guideline, p. 116, item 2, Other Drugs (2)). Regarding Ginkgo Holm and vitamin E that have been recently used as dementiatherapeutic drugs, an RCT directed to MCI patients shows a result that neither dementia prophylactic effect nor prophylactic effect against conversion to Alzheimer was obtained (see the guideline, p. 116, item 2, Other Drugs (3) and (4)). In addition, it is reported that vitamin E and donepezil do not affect conversion from MCI to Alzheimer (see Non-patent Document 3).

For the foregoing reasons, there is neither an effective drug for preventing conversion from MCI to dementia nor a technique or an agent effective for MCI treatment, and early development of prophylactic and therapeutic agent for MCI is needed.

Cilostazol is an antiplatelet drug marketed as a trade name "Pletal" from Otsuka Pharmaceutical Co., Ltd., and there are a large number of other generic drugs of the antiplatelet drug. Cilostazol inhibits thrombus formation and induces vasodilation. Thus, it is well known that cilostazol is used for treatment of cerebral infarction (see Non-patent Document 4), and protects vascular endothelia (see Non-patent Document 5) and improves bloodstream through vasodilation irrespective of endothelia (see Non-patent Document 6). In addition, it is also known that cilostazol reduces accumulation of amyloid β (hereinafter may simply referred to as "Aβ") protein.

Applications of cilostazol to specific diseases are shown in several documents showing application for treatment of amyloid β protein inducible cognitive impairment and treatment of Alzheimer's disease (see Non-patent Document 7) and effectiveness for treatment of dementia (see Non-patent Document 8). It is also known that cilostazol inhibits amyloid β protein inducible memory impairment and oxidation stress (see Non-patent Document 9). Patent Document 1 shows that the use of cilostazol enables treatment of Alzheimer's disease. These documents, however, only examined therapeutic effects by using model animals, and demonstrated no therapeutic effects of cilostazol on humans.

On the other hand, Non-patent Document 10 describes that administration of cilostazol to Alzheimer's patients can reduce deterioration of cognitive function. However, no change is observed in mini-mental state examination (MMSE), and significant variations are found in other evaluations (ADAS-Jcog, WMS-R, and TMT-A) on cognitive function of Alzheimer's patients. Thus, administration of cilostazol to Alzheimer's patients hardly shows improvement. It is shown in the guideline, chapter II, p. 32 that MMSE is the most excellent screening test in a diagnosis of cognitive function. Non-patent Document 11 shows that combined administration of cilostazol and donepezil tends to improve MMSE scores in Alzheimer's patients. This effect, however, is not obtained by cilostazol alone.

That is, the effectiveness of cilostazol alone for treatment of MCI patients based on data has not been substantially shown yet. Although MCI is considered a previous state of various types of dementia and Alzheimer's disease, no effective therapeutic drugs have been found yet.

In the brain of a central nervous system, harmful proteins such as tau protein, synuclein protein, ubiquitinated protein, amyloid protein, and prion protein are accumulated and cause hypofunction of cranial nerves. However, only one of the harmful proteins is less likely to be accumulated in elderly persons. That is, multiple harmful proteins are accumulated in many cases, and the type and degree of this accumulation differ among individuals (see Non-patent Documents 1 to 12).

Such accumulation of harmful proteins are believed to cause cognitive impairment such as MCI. For example, accumulation of amyloid is found in 60-70% of MCI patients (see Non-patent Document 13), and drainage thereof is considered to contribute to prevention and treatment of MCI.

One of drainage pathways commonly used for such harmful proteins is drainage through perivascular lymph drainage pathway (interstitial flow) (see Non-patent Document 14), but neither a technique nor an agent for sufficiently activating the perivascular lymph drainage pathway (interstitial flow) has been found yet.

CITATION LIST

Patent Document

PATENT DOCUMENT 1: Japanese Japanese Patent No. 4590397

Non-Patent Document

Non-patent Document 1: Saito Y and Murayama S, Neuropathology of mild cognitive impairment, Neuropathology (2007) 27(6), 578-584
Non-patent Document 2: Psychiatria et Neurologia Japonica (2011) volume 113, No. 6, pp. 584-592
Non-patent Document 3: The New England Journal of Medicine (Jun. 9, 2005) vol. 352 No. 23, pp. 2379-2388
Non-patent Document 4: Br J Pharmacol (2011) 72, 634-646/Lancet Neurol (2010) 9, 959-968
Non-patent Document 5: Stroke (2012) 43, 499-506
Non-patent Document 6: Stroke (1989) 20, 668-673
Non-patent Document 7: Biochem Biophys Res Commun (May 20, 2011) 408(4), 602-8
Non-patent Document 8: Jpn J Radiol (2010) 28, 266-272
Non-patent Document 9: Br J Phannacol (December, 2010) 161(8), 1899-912
Non-patent Document 10: Geriatr Gerontol Int (2013) 13, 90-97
Non-patent Document 11: Am J Geriatr Psychiatry 17:4 (April 2009) pp. 353-354
Non-patent Document 12: Johnson W G., Late-onset neurodegenerative diseasesthe role of protein insolubility, J Anat (2000) (Pt 4), 609-616
Non-patent Document 13: Proceedings of the Annual Meeting of the Japanese Research Group on Senile Dementia (2011) vol. 18, pp. 84-88
Non-patent Document 14: Weller R O, Djuanda E, Yow H Y, and Carare R O, Lymphatic drainage of the brain and the pathophysiology of neurological disease, Acta Neuropathol (2009) 117(1), 1-14

SUMMARY OF THE INVENTION

Technical Problem

Since it is extremely difficult to regenerate irreversibly altered neurons, new techniques and therapeutic drugs for promoting drainage of harmful proteins accumulated in the brain and for maintaining and improving cranial nerve functions in elderly persons with normal cognitive function or patients with mildly impaired cognitive function have been keenly required. In particular, there are no effective techniques and agents for preventing conversion from MCI to dementia, and early development of prophylactic and therapeutic agents for MCI has been needed.

It is therefore an object of the present invention to provide a prophylactic and/or therapeutic agent for mild cognitive impairment that can improve interstitial flow in sites around cerebral blood vessels in order to excrete harmful proteins in a central nervous system sufficiently through a drainage pathway, and an interstitial flow-improving agent. In particular, an object of the present invention is to provide a cerebrovascular lymph drainage pathway (interstitial flow) improving drug that can sufficiently promote drainage of harmful proteins in a central nervous system in order to maintain and improve the function of cranial nerves in MCI patients. This drug is applicable as a prophylactic and/or therapeutic drug for MCI.

The drainage of harmful proteins by the interstitial flow is not a drainage system through a protein-specific receptor or antigen-antibody reaction but a general drainage system common to all the proteins. Harmful proteins herein are proteins that have lost or declined their inherent functions, and not only futile with respect to the function of central neurons but also actively harmful: Examples of harmful proteins include tau protein, svnuclein protein, prion protein, amyloid protein, and ubiquitinated protein.

Solution to the Problem

The inventors of the present invention have intensively studied to find that a compound useful for prevention and treatment of MCI by improving interstitial flow around blood vessels and excrete harmful proteins in a central nervous system is a compound expressed by general formula (1):

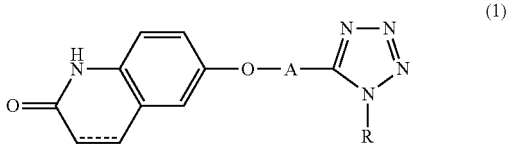

(1)

wherein A is a straight-chain alkylene group having a carbon number of 1 to 6, R is a cycloalkylaryl group having a carbon number of 3 to 8, and a bond between 3- and 4-positions of a carbostyril skeleton is a single bond or a double bond. The inventors proved that the compound enables prevention and treatment of diseases caused by accumulation of harmful proteins, including MCI, whose effective treatment has not been found. The inventors conducted further intensive studies, and completed the invention.

Advantages of the Invention

According to the present invention, a cerebrovascular lymph drainage pathway (interstitial flow is improved so that harmful proteins in a central nervous system can be sufficiently excreted. Thus, it is possible to prevent and/or treat deterioration of the function of cranial nerves caused by accumulation of harmful proteins, including MCI, whose effective treatment has not been found. Medicines obtained according to the present invention will achieve further social contributions by enhancement of quality of life of elderly persons, reduction of care burden, reduction of medical expenses, etc. in the present age facing aging society.

BRIEF DESCRIPTION OF THE DRAWINGS

FIG. 3A shows an AIR group, and FIG. 3B shows a $CO_2$ group.

FIG. 4A shows an AIR group, and FIG. 4B shows a $CO_2$ group.

FIG. 13A shows frontal lobe, and FIG. 13B shows hippocampus.

FIG. 14A shows frontal lobe, and FIG. 14B shows hippocampus.

DESCRIPTION OF EMBODIMENTS

Figure 1:
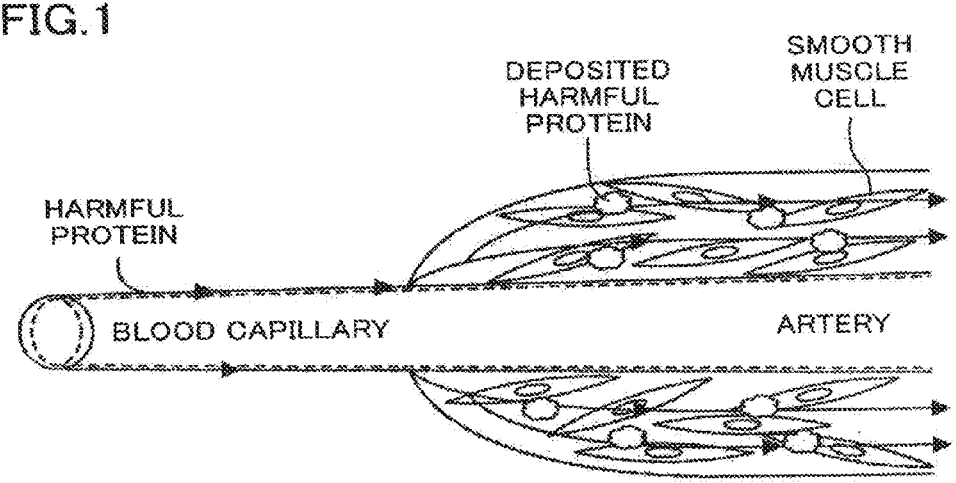
FIG. 1 is a conceptual view illustrating a state in which a drainage mechanism is inhibited by accumulation of harmful proteins deposited on a drainage pathway of interstitial fluid around blood vessels.

An embodiment of the present invention will be specifically described hereinafter with reference to the accompanying drawings. The embodiment is for the purpose of facilitating understanding of the principle of the present invention. The scope of the present invention is not intended to be limited to the embodiment below. Those skilled in the art will make substitutions to the embodiments when necessary without departing the scope of the present invention.

The present invention provides an interstitial flow-improving agent and a prophylactic and/or therapeutic agent for diseases, especially MCI, caused by degradation of function of cranial nerves due to accumulation of harmful proteins.

(1) Interstitial Flow-Improving Agent

According to the present invention, an interstitial flow-improving agent that can improve a cerebrovascular interstitial flow is provided. The "interstitial flow" herein is also called bulk flow, and refers to a flow of interstitial fluid in which metabolite of neurons flows in intercellular space and is finally collected in a peri vascular site and then drained to the outside of the brain through a perivascular drainage pathway (a brain interstitial flow pathway parallel to an intracerebral vascular network), which is a drainage system, particularly interstitial flow in a pathway along basement membranes of smooth muscle cells in vascular media. In the brain, which includes no lymphatic vessels, this pathway is considered to be important for drainage of waste products including harmful proteins.

The "interstitial flow improvement" herein refers to improvement, achieved by some techniques, of interstitial flow impeded by accumulated harmful proteins. In particular, in this description, the "interstitial flow improvement" refers to improvement of interstitial flow in a cerebrovascular site.

An interstitial flow-improving agent according to the present invention as stated below can improve interstitial flow and sufficiently excrete harmful proteins in a central nervous system, especially a cerebrovascular site.

(1-1) Compound

An interstitial flow-improving agent according to this embodiment employs, as an active ingredient, a carbostyril derivative (hereinafter referred to as compound (1)) represented by general formula (1) below or a salt thereof.

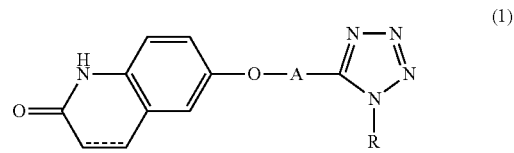

In general formula (1), A is a straight-chain alkylene group having a carbon number of 1 to 6, R is a cycloalkylaryl group with a carbon number of 3 to 8, and the bond between the 3- and 4-positions of a carbostyril skeleton is a single bond or a double bond.

Specifically, A is a methylene group, an ethylene group, a propylene group, an n-butylene group, an n-pentylene group, or an n-hexylene group, and preferably an n-butylene group.

Specifically, R is a cyclopropyl group, a cyclobutyl group, a cyclopentyl group, a cyclohexyl group, a cycloheptyl group, or a cyclooctyl group, and preferably a cyclohexyl group.

It is preferable that in the compound (1), A is an n-butylene group, R is a cyclohexyl group, and the bond between the 3- and 4-positions of a carbostyril skeleton is a single bond. In this case, the interstitial flow-improving agent of the present invention includes 6-[4-(1-cyclohexyl-1H-tetrazole-5-yl)butoxy]3,4-dihydrocarbostyril (cilostazol) or a salt thereof as an active ingredient.

The interstitial flow-improving agent of this embodiment can improve interstitial flow flowing in cerebral blood vessel wall (i.e., flowing in intercellular space and finally flowing in a vascular wall to be excreted) so as to excrete harmful proteins in a central nervous system sufficiently. As described below, the clearance (excretion) of harmful proteins in the central nervous system herein refers to drainage of harmful proteins through a drainage pathway of perivascular interstitial fluid. The drainage pathway is a pathway for interstitial flow along basement membranes of smooth muscle cells in vascular media.

The interstitial flow-improving agent of this embodiment is also applicable not only to humans but also mammals such as monkeys, calfs, horses, swine, sheep, canines, felines, rats, and mice.

A salt can be produced from the compound (1) by allowing pharmaceutically acceptable acid to act. Examples of acids that can act are not specifically limited as long as the obtained salt is pharmacologically acceptable, and include: inorganic acid such as sulfuric acid, phosphoric acid, hydrochloric acid, and hydrobromic acid; and organic acid such as oxalic acid, maleic acid, fumaric acid, malic acid, tartaric acid, citric acid, and benzoic acid.

(1-2) Dosage Form

The interstitial flow-improving agent of this embodiment can be pharmaceutical products for oral administration such as tablets, granules, subtle granules, or capsules, various liquid pharmaceutical products suitable for oral administration, and pharmaceutical products for oral administration such as injections or suppositories.

In the case of a pharmaceutical product for oral administration, the interstitial flow-improving agent of this embodiment can be obtained as a pharmaceutical product from, for example, impalpable powder of the compound (1) or a salt thereof, a disperser, and/or a solubility improving agent together with a pharmaceutical product carrier, in the form of tablets, granules, subtle granules, capsules, etc. The presence of the disperser and/or the solubility improving agent can enhance the dispersibility and/or dissolution and absorption ability of impalpable powder of the compound (1) or a salt thereof.

Examples of the pharmaceutical product carrier include an excipient, a binder, a disintegrator, a lubricant, and a plasticizer. Examples of the excipient include saccharose, sodium chloride, mannitol, lactose, glucose, starch, calcium carbonate, kaolin, microcrystalline cellulose, low substituted hydroxypropylcellulose, hydroxypropylmethylcellulose acetate succinate, and silicate. Examples of the binder include water, ethanol, propanol, glucose solution, starch solution, liquefied gelatin, sodium carboxymethylcellulose, methylcellulose, hydroxypropylcellulose, hydroxypropylmethylcellulose, polyvinyl alcohol, and polyvinyl pyrrolidone. Examples of the disintegrant include carboxymethylcellulose calcium, dried starch, sodium bicarbonate, calcium carbonate, polyoxyethylene sorbitan fatty acid esters, monoglyceryl stearate, starch, sodium carboxymethylstarch tripolyphosphate, and croscarmellose sodium. Examples of the lubricant include purified talc, stearic acid salts, borax, polyethylene glycol, colloidal silicic acid, and hydrogenated oil. Examples of the plasticizer include glycerin fatty acid ester, dioctyl phthalate, dibutyl phthalate, triacetin, triethyl citrate, and castor oil.

Examples of the disperser and/or the solubility-improving agent include water-soluble polymers and surfactants. Examples of the water-soluble polymers include hydroxypropylcellulose, polyvinyl alcohol, polyvinyl pyrrolidone, hydroxypropylmethylcellulose, carboxymethylcellulose, and polyacrylic acid. Examples of the surfactants include: alkyl sulfates such as sodium lauryl sulfate, and magnesium lauryl sulfate; polyglycerol fatty acid esters such as decaglyceryl monolaurate, and decaglyceryl monomyristate; polyoxyethylene sorbitan fatty acid esters such as polyoxyethylene sorbitan monooleate; polyethylene glycol fatty acid esters such as polyoxyethylene monostearate; polyoxyethylene alkylether such as polyoxyethylene lauryl ether; polyoxyethylene castor oil such as polyoxyethylene hydrogenated castor oil and hydrogenated castor oil; sucrose fatty acid esters such as sucrose ester stearate and sucrose palmitate.

In the case of producing an oral pharmaceutical product by using materials of the above examples, 0.001 to 100 parts by weight, preferably 0.01 to 10 parts by weight, of the disperser and/or the solubility improving agent is added with respect to one part by weight of impalpable powder of the compound (1) or a salt thereof. If the amount of the disperser and/or the solubility improving agent is smaller than 0.001 part by weight, abroption is poor, whereas if the amount of the disperser and/or the solubility improving agent is larger than 100 parts by weight, there is a possibility of restriction because of toxicity such as a mucous membrane disorder or under the Pharmaceutical Affairs Law.

To prepare tablets, impalpable powder of the compound (1) or a salt thereof is made in the form of tablets with an ordinary method by using the pharmaceutical product carrier. Granules or subtle granules can be prepared by adding the pharmaceutical product carrier to impalpable powder of the compound (1) or a salt thereof and granulating the mixture with, for example, a fluidized-bed granulation method, a high-speed stifling granulation method, a stirring fluidized-bed granulation method, a centrifugal flow granulation method, an extrusion granulation method. Encapsulated formulation is mixed with an inert medicinal filler or diluent for preparation, and are placed in hard gelatin capsules or soft capsules.

The impalpable powder of the compound (1) or a salt thereof used in the interstitial flow-improving agent of this embodiment has an average particle size of generally 8 μm or less, preferably 4 μm or less. The impalpable powder having such an average particle size may be formed by using, for example, a hammer mill, a jet mill, a rotary ball mill, a vibration ball mill, a shaker mill, a rod mill, and a tube mill.

The interstitial flow-improving agent of this embodiment may be obtained by coating tablets, granules, or subtle granules containing the compound (1) or a salt thereof with a controlled-release coating base material. Examples of the controlled-release coating base material include cellulose acetate phthalate, hydroxypropylmethylcellulose phthalate, methacrylic acid copolymer, and ethyl cellulose. Thus, in a lower part of the digestive tract, elution of the compound (1) or a salt thereof can be obtained.

The oral liquid pharmaceutical product is prepared by mixing the compound (1) or a salt thereof with a sweetener (e.g., sucrose), a preservative (e.g., methylparaben or propylparaben), a coloring agent, or a perfume, for example.

A pharmaceutical product for injection among pharmaceutical products for parenteral administration is prepared in the form of, for example, a solution, an emulsion, or a suspension, and is rendered isotonic with blood. The pharmaceutical product in the form of a solution, an emulsion, or a suspension is prepared by using, for example, an aqueous solvent, ethyl alcohol, propylene glycol, ethoxylated isostearyl alcohol, polyoxylated isostearyl alcohol, or polyoxyethylene sorbitan fatty acid ester. Examples of the aqueous solvent include water and a medium containing water. Water used in this case is sterile water. Examples of the medium containing water include physiologic saline, phosphate-buffered physiologic saline (PBS), and lactic acid-added Ringer solution.

In the pharmaceutical product for injection, the content of the compound (1) or a salt thereof is not specifically limited and varies depending on the purpose of the pharmaceutical product, and is, for example, 0.01 to 10 mg/mL, preferably 0.05 to 5 mg/mL.

For the pharmaceutical product for injection, additives generally used in the art may be used as necessary. Examples of the additive include a tonicity adjusting agent, a stabilizer, a buffer, a preservative, a chelating agent, an antioxidant, and a solubilize. Examples of the tonicity-adjusting agent include sugars such as glucose, sorbitol, and mannitol, sodium chloride, glycerin, propylene glycol, and polyethylene glycol. Examples of the stabilizer include sodium sulfite. Examples of the buffer include a boric acid buffer, a phosphate buffer, a citrate buffer, a tartaric acid buffer, and an acetate buffer. Examples the preservative include p-hydroxybenzoate ester, benzyl alcohol, chlorocresol, phenethyl alcohol, and benzethonium chloride. Examples of the chelating agent include sodium edetate and sodium citrate. Examples of the antioxidant include sodium sulfite, sodium bisulfite, sodium ascorbate, and sodium thiosulfate. Examples of the solubilizer include dextran, polyvinyl pyrrolidone, sodium benzoate, ethylenediamine, salicylic acid amide, nicotinamide, and polyoxyethylene hydrogenated castor oil derivatives.

The pharmaceutical product for injection may include a pH adjustor. The pH adjustor may be acids or bases. Specifically, examples of the acids include ascorbic acid, hydrochloric acid, gluconic acid, acetic acid, lactic acid, boric acid, phosphoric acid, sulfuric acid, tartaric acid, and citric acid. Examples of the bases include potassium hydroxide, calcium hydroxide, sodium hydroxide, magnesium hydroxide, monoethanol airtime, diethanol aminne, and triethanol aminne.

The administration amount of the compound (1) or a salt thereof itself as an active ingredient in the interstitial flow-improving agent of this embodiment can be appropriately determined depending on the age, sex, weight, and symptom, for example, of a patient. For example, a single dose or two to several doses of 10 to 400 mg, preferably 100 to 200 mg, can be administered to an adult (weight 50 kg) in one day.

(1-3) Concomitant Drug

The interstitial flow-improving agent of this embodiment may be used with memantine hydrochloride, which is an NMDA acceptor antagonist. The interstitial flow-improving agent may be used with a β-secretase inhibiter, a γ-secretase inhibiter, a neprilysin activator, or an Aβ protein vaccine.

The type of the β-secretase inhibitor may be, but is not limited to, OM99-2, GT-1017, or $P_{10}$-$P_4$'staV, for example. The type of the γ-secretase inhibitor may be, but is not limited to, (S,S)-2-aminocyclopentanecarboxylic acid (ACPC) or Semagacestat, for example. The neprilysin activator is a synthetic agonist to a somatostatin acceptor, for example. The Aβ protein vaccine may be either a passive immunity vaccine for direct administration of antibodies or an active immunity vaccine for administration of Aβ peptide with an adjuvant.

For example, it is reported that a vaccine of an intramuscular injection type as a mixture of synthetic $Aβ_{1-42}$ and adjuvant QS21 induces subacute meningoencephalitis as a side effect in about 6% of vaccinators, but the combined use of the interstitial flow-improving agent of this embodiment and an Aβ protein vaccine whose dosage is restricted is expected to reduce the side effect to some degree and improve Aβ-related diseases. In the case of the γ-secretase inhibitor, for example, segmentation of other elements such as Notch1 might be inhibited. It is known that Notch1 is related to differentiation of immune cells in adults and inhibition of the differentiation causes an immune disorder. The combined use of the γ-secretase inhibitor whose dosage is reduced and the interstitial flow-improving agent of this embodiment is expected to reduce a side effect to some degree and improve Aβ-related diseases.

(1-4) Action Mechanism of Improvement of Interstitial Flow

First, cAMP responsive element binding protein (CREB) is closely related to higher brain functions such as space perception and long-term memory, and is activated when being phosphorylated. A known action mechanism in which cilostazol inhibits deposition of Aβ is that Aβ has the function of inhibiting phosphorylation of CREB and cilostazol can facilitate phosphorylation of CREB, or that cilostazol adjusts the expression level of ApoE protein related to agglutination of Aβ and reduction of the stress level of intracerebral oxidation can also inhibit deposition of Aβ and prevent deterioration of the cognitive function.

On the other hand, the interstitial flow-improving agent of this embodiment improves interstitial flow and, thereby, sufficiently excretes harmful proteins in central nervous systems. The mechanism of this interstitial flow improvement will now be described using Aβ, a typical harmful substance in the brain, as an example.

There are a large number of pathways in which Aβ produced is removed from the brain along with interstitial flow, and although the proportion of function of the pathways varies depending on, for example, the state and location of Aβ, pathways are mainly, for example, as follows:
(i) drainage through blood brain barrier (BBB),
(ii) drainage through a drainage pathway of perivascular interstitial fluid; and
(iii) decomposition by neprilysin, which is an Aβ decomposition enzyme, and uptake of Aβ by astrocyte and microglia.

Figure 2:
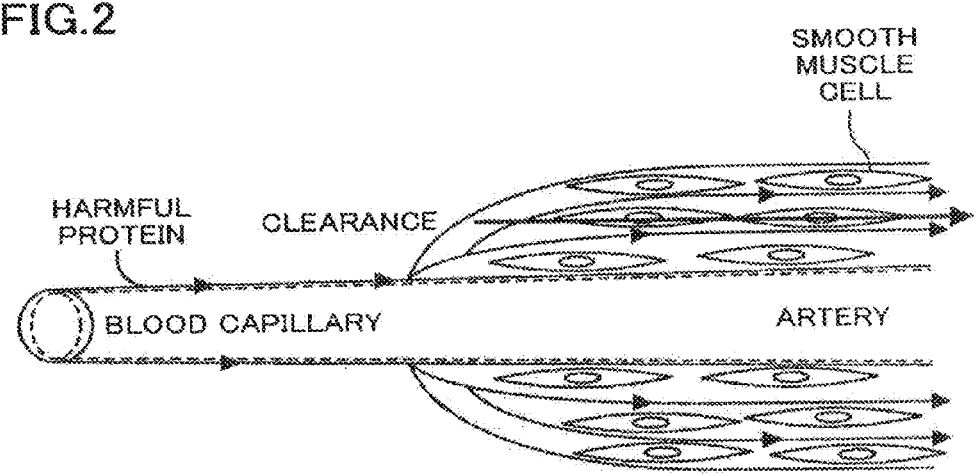
FIG. 2 is a conceptual view illustrating a state in which a flow of interstitial fluid around blood vessels is improved in a drainage pathway so that harmful proteins are excreted.

As illustrated in FIG. 1, harmful proteins such as Aβ are deposited on the vascular smooth muscle cell layer on the vascular wall and, thereby, inhibit the function of smooth muscle cells, resulting in reduction of beating of blood vessels, which is a driving force of an interstitial fluid, and inhibition of drainage of harmful proteins through interstitial fluid. Thus, clearance of harmful proteins is inhibited, and agglutination of Aβ occurs, thereby forming amyloid fibrils, for example. However, as illustrated in FIG. 2, the interstitial flow-improving agent of this embodiment improves interstitial flow passing through a pathway along the basement membrane of smooth muscle cells on the media, and promotes drainage of harmful proteins through interstitial fluid. Thus, an increase in concentration of harmful proteins is less likely to occur so that no agglutination of Aβ occurs and formation of amyloid fibrils is reduced.

Specifically, a feature of the present invention is in that a carbostyril derivative such as cilostazol improves interstitial flow passing through a pathway along the basement membrane of smooth muscle cells in the vascular media so that drainage of harmful proteins in the brain through interstitial fluid is promoted. Since the drainage of harmful proteins through the interstitial flow is a general drainage system irrespective of the type and amount of proteins, Aβ herein is merely an example of intracerebral harmful proteins to be drained by improving the interstitial flow.

In Down's syndrome, which is caused by the presence of an extra chromosome 21 in somatic cells, i.e., three chromosomes 21 (trisomy syndrome), APP is on the chromosome 21, and β-secretase (BACE-2) genes, which generate Aβ, are also on the chromosome 21. Thus, APP is excessively copied and, consequently, formation of an amyloid plaque starts. Since the interstitial flow-improving agent of this embodiment can improve the interstitial flow and promote drainage of Aβ produced through the interstitial fluid, formation of amyloid fibrils is reduced, thus enabling improvement of Down's syndrome.

In addition, in the course of development of vertebrates, retinas are originated from optic vesicles as a laterally projecting part of diencephala, and retinas are part of the brain embryologically. APP come to be strongly expressed in retina ganglion cells with age, and similarly to the brain, it is known that production and accumulation of Aβ are possibly observed in the retinas. Since the interstitial flow-improving agent of this embodiment can improve the interstitial flow and promote drainage of Aβ through interstitial fluid, formation of amyloid fibrils is reduced, and thereby, age-related macular degeneration can be improved.

The age-related macular degeneration is not related to neovessels, and classified into an atrophia type having atrophia of retinal pigment epithelial cells and choriocapillaris and an effusion type related to neovessels. In these types, the effusion type can be a problem because this type induces a severe visual disorder. In the effusion type, damage caused by, for example, reactive oxygen causes part of retinal cells to be peeled off, and drusen as harmful protein is deposited along the basal surfaces of retinal pigment epithelia. The deposition of drusen facilitates generation of neovessels from the depth of retina, and bleeding and effusion occur from neovessels with proliferative tissues to maculae of retina, and finally cicatrization occurs, resulting in a significant decrease in vision and central scotoma. In drusen of age-related macular degeneration patients, Aβ is highly frequently present, and a common pathologic crisis mechanism exists between age-related macular degeneration and cerebral amyloid angiopathy. Thus, since the interstitial flow-improving agent of this embodiment can improve the interstitial flow and promote drainage of Aβ produced through interstitial fluid, age-related macular degeneration can be improved.

In addition, Lewy body disease is a disease caused by accumulation of causal protein of a synuclein in neurons. In the brain suffering from this disease, Aβ is highly frequently accumulated (which is called "usual" Lewy body disease), and accumulation of two types of causal proteins, Aβ and α synuclein, synergistically contribute to the stages of this crisis (see "Examining the mechanisms that link β-amyloid and α-synuclein pathologies," Alzheimers Res Ther. 2012 Apr. 30; 4(2): 11). Thus, in Lewy body disease, activation of the interstitial flow to promote drainage of harmful proteins can inhibit accumulation of Aβ and α synuclein, and thereby, the crisis can be prevented and the progress thereof can be reduced.

(1-5) Application

Specific application of the interstitial flow-improving agent of this embodiment is not specifically limited, and as specifically described in "(1-4) Action Mechanism" above, the interstitial flow-improving agent is intended to treat and prevent all the types of diseases that can be prevented or treated by improving interstitial flow and promote drainage of harmful proteins through interstitial fluid. Examples of such diseases include diseases related to accumulation of harmful proteins in the central nervous system, e.g., mild cognitive impairment, cerebral amyloid angiopathy, frontotemporal dementia, Down's syndrome, macular degeneration, Lewy body disease, Parkinson's disease, and amyotrophic lateral sclerosis. The interstitial flow-improving agent of the present invention can be used for preventing and/or treating these diseases.

In particular, the interstitial flow-improving agent of the present invention including the compound (1), especially cilostazol, is very useful as a prophylactic and/or therapeutic agent for MCI, which will be specifically described in section (2) below.

(2) Prophylactic and/or Therapeutic Drug for MCI (2-1) Compound

The prophylactic and/or therapeutic drug for MCI of this embodiment uses the compound (1) or a salt thereof described in the section "(1) Interstitial Flow Improving Agent" above, as an active ingredient. The compound is similar to that described in section (1-1) above. The prophylactic and/or therapeutic drug for MCI of the present invention is applicable not only to humans, but also to mammals such as monkeys, calfs, horses, swine, sheep, canines, felines, rats, and mice.

(2-2) Mild Cognitive Impairment (MCI)

The term "MCI" herein has been already described in the section of "Background" of the specification. More specifically, MCI generally refers to a disease defined based on the MCI criterion in "Guidelines for Management of Dementia" described above irrespective of the type and amount of accumulated harmful proteins, and an MCI patient refers to a patient showing such a symptom.

The prophylactic and/or therapeutic drug for MCI of the present invention is especially effective for MCI patients having scores of 22-26 in mini-mental state examination (MMSE). Specifically, a prophylactic and/or therapeutic drug for MCI according to the present invention, which will be described below, is effectively used for patients defined as MCI patients based on the MCI criterion in "Guidelines for Management of Dementia," and especially for MCI patients having MMSE scores of 22-26.

Among such MCI patients, the prophylactic and/or therapeutic drug for MCI of the present invention is more significantly effective for elderly persons of 60 years of age or more, more preferably 75 years of age or more.

As a substantial index of scores in mini-mental state examination (MMSE) frequently employed in this field as a value indicating cognitive function, scores of 22 to 26 are levels of suspected mild cognitive impairment as described above. In addition, scores over 20 is a level at which independence is maintained (i.e., not dementia) and scores less than or equal to 20 is a level of suspected dementia. Scores under 14 are a level requiring a conservator, and scores between 14 and 20, inclusive, are a level requiring a curator or a supporter. That is, increase in MMSE score by about 1 to 2 is not significantly effective, but increase in MMSE score by about 4 eliminates the necessity of a curator or a supporter or enables independence, and thus, is significantly effective.

The number of patients suffering from mild cognitive impairment (MCI) drastically increases with aging of the population. In view of this, it is very important to prevent transition to dementia by treating MCI patients for prophylaxis of irreversible alteration of cranial nerves. In dementia patients suffering from irreversible neurodegeneration, the possibility of cure is very low, but MCI patients might be cured or have their MCI symptoms stable, or might transition to different symptoms from MCI. It has been demonstrated that harmful proteins such as synuclein and Aβ start accumulating in the brain in MCI patients and even in elderly persons having normal cognitive functions. Although the importance of early treatment for elimination of harmful proteins or prevention of accumulation are recognized, there are currently no effective therapeutic drugs, as described in the section of "Background." Because of such a situation, MCI is known as a disease discriminated from various known types of dementia, in addition, since no prophylactic effects are found in known dementia therapeutic/prophylactic drugs, a new pharmaceutical product that can prevent or treat MCI has been keenly needed.

Figure 17:
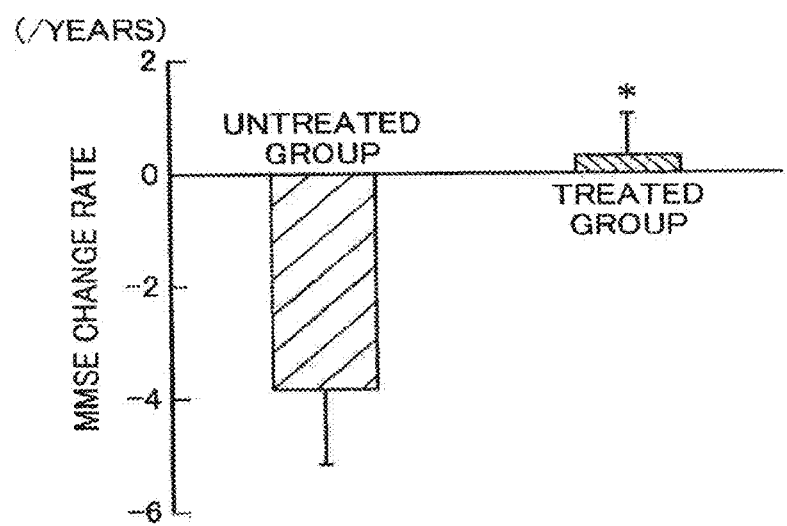
FIG. 17 is a graph showing a change rate of MMSE scores of a cilostazol-administered group and a non-administered group in an MCI patient group.

The use of the prophylactic and/or therapeutic drug for MCI of the present invention can achieve treatment of MCI and prevent conversion to various types of dementia, and is also expected to improve or maintain the cognitive function of elderly persons having normal cognitive functions, as well as MCI patients. In particular, examples below show that consecutive oral administration of cilostazol, which is an active ingredient of the prophylactic and/or therapeutic drug for MCI of the present invention, significantly improves cognitive function of MCI patients (see, for example, FIG. 17). This is a significant advantage of the present invention unexpected from known circumstances. Thus, the prophylactic and/or therapeutic drug for MCI of the present invention can be a very useful new drug.

Regarding the cognitive function as stated herein, the cognitive function in dementia refers to the cognitive function with cognitive impairment given a diagnosis of dementia by a doctor, and including a case of dementia with a mild cognitive impairment and a case of dementia with a severe cognitive impairment. The cognitive function in the case of MCI is a cognitive function with cognitive impairment not so severe as to cause dementia. Thus, the cognitive function can be classified into normal cognitive function, MCI, mild dementia, and severe dementia, which are listed in the order from a normal condition to a functional impairment condition. In the field of dementia, scores based on mini-mental state examination (MMSE) are preferably used as an index of cognitive function as described above. The prophylactic andior therapeutic drug for MCI of the present invention is effective especially for MCI patients showing cognitive function with MMSE scores of 22 to 26 as described above. Among these MCI patients, the prophylactic and/or therapeutic drug for MCI of the present invention is especially effective for elderly persons of 60 years of age or more. Specifically, a known AD therapeutic drug improves only a small degree of MMSE scores (where the difference between the value of a treated group and the value of an untreated group is about one at most). On the other hand, as specifically described in Example (4), the prophylactic and/or therapeutic drug for MCI of the present invention shows a significantly high degree of advantage, i.e., increases MMSE scores by about 4. In particular, the prophylactic and/or therapeutic drug for MCI of the present invention shows significant improvement in items requiring a high level of cognitive function in MMSE items, i.e., items requiring cognitive domains prone to be involved in neurodegenerative diseases, such as item 1: orientation to time, item 5: delayed recall, item 9: command with sentence, and item 11: visual configuration. The prophylactic and/or therapeutic drug for MCI of the present invention, however, does not show such significant improvement for dementia patients (especially patients with MMSE scores under 21) as specifically described in Example (5) below.

Cerebral amyloid angiopathy goes through MCI as its precursor stage. It is reported that an MCI case in which microbleeds caused by cerebral amyloid angiopathy is observed on image shows the rate of transition to dementia 2.6 times as high as that of a case without microbleeds (see Staekenhorg S S, et al. Stroke 2009). Lewy body-type dementia occupies a certain percentage of the precursor stage of MCI (see "Mild cognitive impairment associated with underlying Alzheimer's disease versus Lewy body disease" Parkinsonism Relat Disord. 2012 January; 18 Suppl 1: S41-4). Thus, an early treatment in the MCI stage can obviate transition to diseases such as dementia from cerebral amyloid angiopathy and Lewy body disease.

(2-3) Concomitant Drug

The prophylactic and/or therapeutic drug for MCI of the present invention may include a combination of the compound (1) or a salt thereof and an acetylcholinesterase inhibiter, as active ingredients.

In the compound (1) described above, it is preferable that A is n-butylene, R is cyclohexyl, the bond between the 3- and 4-positions of a carbostyril skeleton is a single bond. In this case, the MCI improving drug of the present invention includes a combination of 6-[4-(1-cyclohexyl-1H-tetrazole-5-yl)butoxy]3,4-dihydrocarbostyril (cilostazol) or a salt thereof and an acetylcholinesterase inhibiter.

The acetylcholinesterase inhibiter may be, but is not limited to, donepezil hydrochloride, rivastigmine tartrate, galantamine hydrobromide, or memantine hydrochloride, for example, and is preferably donepezil hydrochloride.

The combined administration of the compound (1) or a salt thereof and the acetylcholinesterase inhibiter may be, but is not limited to, as follows, for example. In the following examples, C is the compound (1) or a salt thereof, and A is the acetylcholinesterase inhibiter. That is, (i) administration of a single pharmaceutical product obtained by formulating C and A at the same time, (ii) coadministration in an identical administration pathway of two pharmaceutical products obtained by individually formulating C and A, (iii) time varied administration in an identical administration pathway of two pharmaceutical products obtained by individually formulating C and A, (iv) coadministration in different administration pathways of two pharmaceutical products obtained by individually formulating C and A, and (v) time varied administration in different administration pathways of two pharmaceutical products obtained by individually formulating C and A.

(2-4) Dosage and Dosage Form

The dosage of the prophylactic and/or therapeutic drug for MCI described above can be selected as appropriate on the basis of dosage clinically used. For example, the dosage of cilostazol or a salt thereof is 30 to 400 mg per day in adult which is administered once or being divided in two to several times. The dosage of donepezil hydrochloride is 1 to 10 mg per day in adult which is administered once or being divided in two to several times.

As described in section (1-2) above, the prophylactic and/or therapeutic drug for MCI of the present invention can be a pharmaceutical product for oral administration, various liquid pharmaceutical products suitable for oral administration, or pharmaceutical products for parenteral administration such as injection and suppository, as well as an interstitial flow-improving agent. That is, the prophylactic and/or therapeutic drug for MCI of the present invention can be in a dosage form similar to that of the "interstitial flow-improving agent" of the present invention.

In the case of combined use with the acetylcholinesterase inhibiter, the mixing ratio between the compound (1) or a salt thereof and the acetylcholinesterase inhibiter can be appropriately selected depending on the administration route, symptom, age, and acetylcholinesterase inhibiter to be used, for example. In general, the mixing ratio is determined based on a general dosage of the acetylcholinesterase inhibiter to be used. For example, the mixing ratio between cilostazol or a salt thereof and donepezil hydrochloride is such that cilostazol or a salt thereof: donepezil hydrochloride is 50:1 to 20:1.

Regarding MCI patients, 70 to 80% of the MCI patients transition to dementia after about five years. However, the present invention can suitably improve MCI, and thus, early treatment of MCI can obviate transition to dementia.

EXAMPLES (1) Enhancement of Vascular Pulsation Driving Force by Cilostazol

In brain interstitial flow in a central nervous system, vascular wall motion caused by vascular pulsation of artery serves as a driving force so that harmful proteins are excreted (see Mechanisms to explain the reverse perivascular transport of solutes out of the brain. J Theor Biol. 2006 Feb. 21; 238(4): 962-74), Dilation of artery in vascular pulsation is caused by an increased blood pressure in artery due to pulsation of heart, and a decrease in dilation ability of artery attenuates vascular wall motion, and also reduces the interstitial flow. In aged mice or in the presence of cerebral amyloid angiopathy, vascular elasticity (flexibility) of cerebral artery significantly decreases and vascular wall motion attenuates, resulting in deterioration of the ability of drainage of harmful proteins (see "Perivascular drainage of solutes is impaired in the ageing mouse brain and in the presence of cerebral amyloid angiopathy," Acta Neuropathol. 2011 April; 121(4): 431-43). The degree of vascular elasticity in cerebral artery can be evaluated by using reactivity with a change in the concentration of blood carbon dioxide. Specifically, cerebral artery whose vascular elasticity and vascular pulsation driving force are maintained, has the ability of sufficiently dilating the vessel diameter afer an increase in the concentration of blood carbon dioxide, and maintains excretion ability for harmful proteins through h interstitial flow. On the other hand, cerebral artery whose vascular elasticity and vascular pulsation driving force are decreased, loses the ability of sufficiently dilating the vessel diameter in response to an increase in the concentration of blood carbon dioxide, and has its escretion ability for harmful proteins impaired. In view of this, as harmful protein-accumulated model animals, model mice (Tg-SwDI mice) showing pathological changes, especially cerebral amyloid angiopathy, (Davis et al, 2004) are used, and the effect of cilostazol on the reactivity of cerebral artery to the concentration of blood carbon dioxide was examined.

In the examination, 16 male Tg-SwDI mice aged 1.5 months were prepared and classified into cilostazol-containing feed administered group (n=9) and ordinary feed administered group (n=7). These mice were grown to the age of 15 months. The cilostazol concentration in cilostazol-containing feed was 0.3 wt %. The Tg-SwDI mice aged 1.5 months are at an initial stage in which accumulation of Aβ in cerebral blood vessels starts, i.e., at an initial stage of cerebral amyloid angiopathy, and it is assumed that necrosis of intracerebral neurons has not progressed significantly.

After 15 months from the start of breeding, with respect to Tg-SwDI mice of the cilostazol-containing feed administered group and Tg-SwDI mice of the ordinary feed administered group, Tg-SwDI mice were placed under inhalation anesthesia using 1-5% isoflurane, and the relative increase rate of the cerebrovascular diameter in Tg-SwDI mice of the cilostazol-containing feed administered group supplied with 5% $CO_2$ and Tg-SwDI mice of the ordinary feed administered group supplied with 5% $CO_2$ was compared. The cerebrovascular diameter was measured with an observation window formed by cutting out a fracture of 5 mm×5 mm from cranial bone, and FITC-dextran was injected through tail veins so that blood vessels be visualized.

Figure 3B:
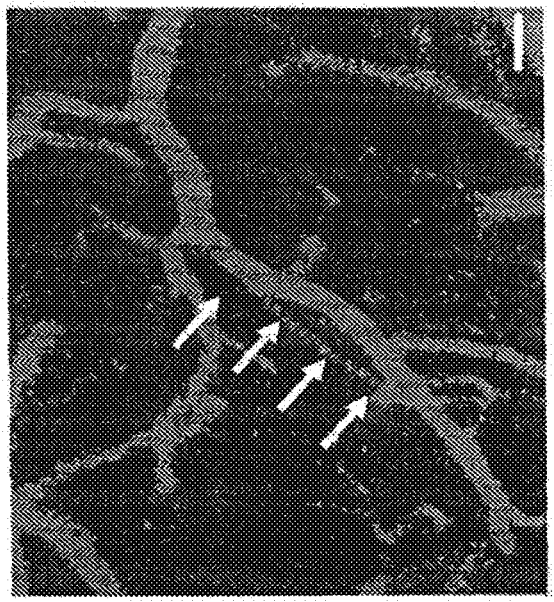
FIGS. 3A and 3B show images cerebral surface vessels in Tg-SwDI mice of an ordinary feed administered group.
Figure 3A:
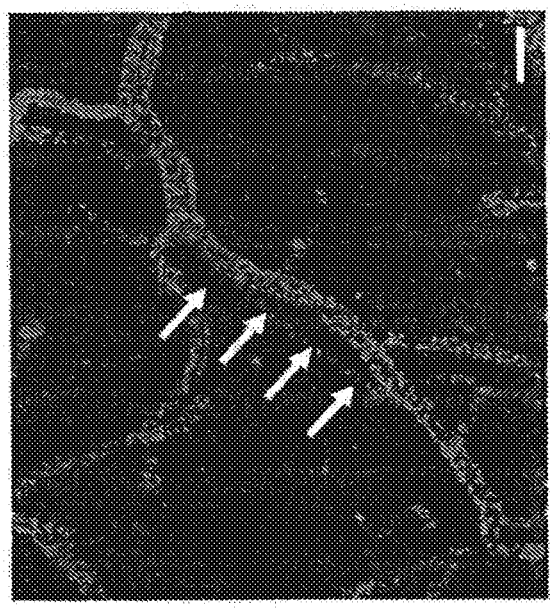
Figure 4B:
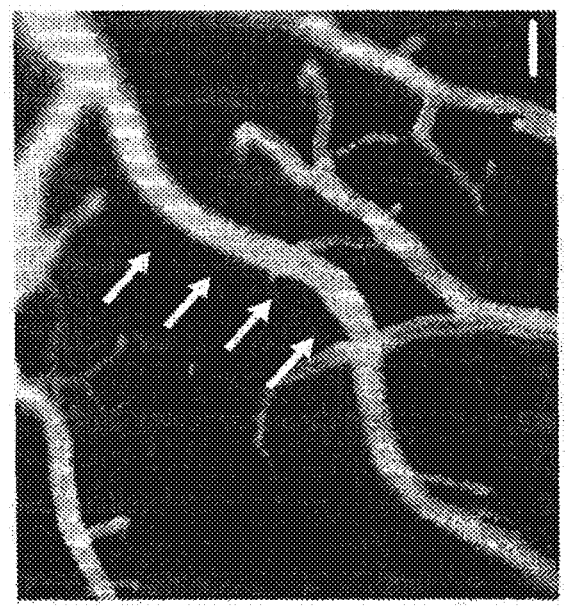
FIGS. 4A and 4B show images cerebral surface vessels in Tg-SwDI mice of a cilostazol-containing feed administered group.
Figure 4A:
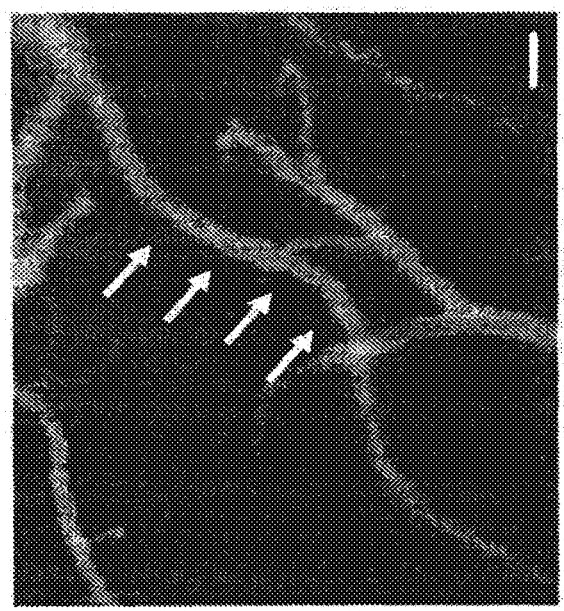
Figure 5:
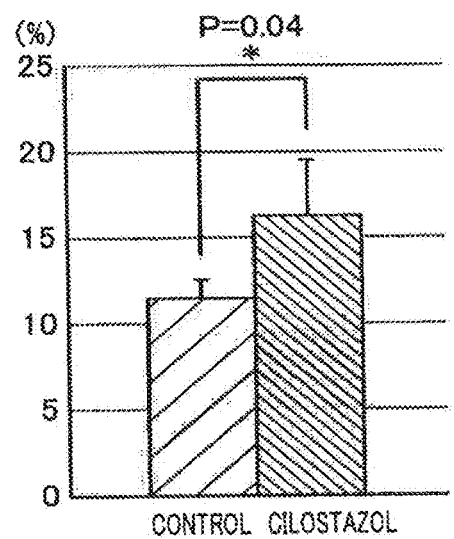
FIG. 5 is a graph showing relative increases in cerebrovascular diameter after $CO_2$ supply in Tg-SwDI mice of a group administered with cilostazol-containing feed for 13.5 months and Tg-SwDI mice of an ordinary feed administered group after 15 months from the start of breeding.

FIGS. 3A and 3B show images of cerebral surface vessels in Tg-SwDI mice of the ordinary feed administered group. FIG. 3A shows a group (an AIR group) supplied with air containing no $CO_2$. FIG. 3B shows a group (a $CO_2$ group) supplied with air containing $CO_2$ in a final concentration of 5%. FIGS. 4A and 4B show images of cerebral surface vessels in Tg-SwDI mice of the cilostazol-containing feed administered group. FIG. 4A shows an AIR group, and FIG. 4B shows a $CO_2$ group. In FIGS. 3A, 3B, 4A, and 4B, the scale bar is 50 μm. As indicated by arrows in FIGS. 3A, 3B, 4A, and 4B, it is clearly shown that in the AIR supply, i.e., the AIR groups, no difference was observed between the cerebral artery diameter of the ordinary feed administered group (FIG. 3A) and the cerebral artery diameter of the cilostazol-containing feed administered group (FIG. 4A) (where the artery diameters of these groups are 18.6±2.35 μm and 18.9±1.10 μm [average±standard error, the same hereinafter], p>0.10). It is also clearly shown that in the $CO_2$ supply, i.e., the $CO_2$ supply groups, dilation of cerebral surface artery vessels by the supply of $CO_2$ is superior in the cilostazol-containing feed administered group (FIG. 4B) to the ordinary feed administered group (FIG. 3B). The examination of the statistic carbon dioxide concentration reactivity demonstrates that administration of cilostazol significantly enhances cerebral artery vasodilation ability with the $CO_2$ supply (see FIG. 5).

Figure 6:
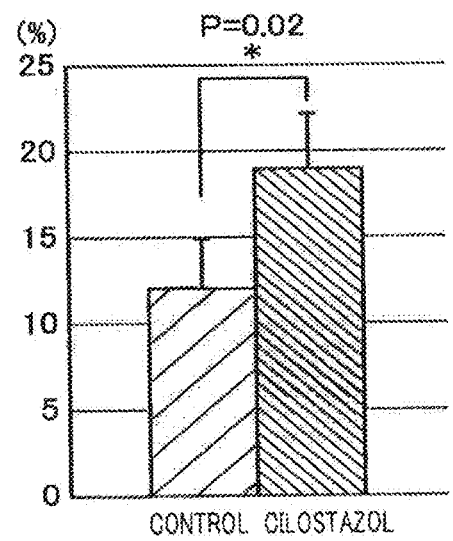
FIG. 6 is a graph showing relative increases in cerebrovascular diameter after $CO_2$ supply in Tg-SwDI mice of a group administered with cilostazol-containing feed for 8 months and Tg-SwDI mice of the ordinary feed administered group after 12 months from the start of breeding.

FIG. 6 shows relative increases in cerebrovascular diameter under a $CO_2$ supply in Tg-SwDI mice of the ordinary feed administered group aged 4 to 12 months after birth and Tg-SwDI mice aged 4 to 12 months after birth and administered with cilostazol-containing feed for 8 months. Similarly to the case of the mice described above, it is clearly shown that no difference was observed between the cerebral artery diameter of the ordinary feed administered group and the cerebral artery diameter of the cilostazol-containing feed administered group before the $CO_2$ supply (where the artery diameters of these groups are 20.0±2.78 μm and 21.3±3.85 μm, p>0.10), and administration of cilostazol significantly increases the cerebral artery vasodilation ability (the relative increase rate of the vessel diameter) by the $CO_2$ supply statistically.

These results show that administration of cilostazol enhances the vascular pulsation driving force as a prime motive force of the brain interstitial flow that is important in a drainage system for harmful proteins.

(2) Harmful Protein Drainage Facilitation by Cilostazol

To verify interstitial flow improvement by cilostazol, harmful protein drainage facilitation by cilostazol was examined by using a cerebral amyloid angiopathy model. Totally unlike a drainage system through a specific receptor or antigen-antibody reaction, drainage of harmful proteins through the interstitial flow is a general drainage system irrespective of the type and amount of proteins, and Aβ in these examples is merely an example of intracerebral harmful proteins for which the interstitial flow is improved so that drainage is facilitated.

Figure 7:
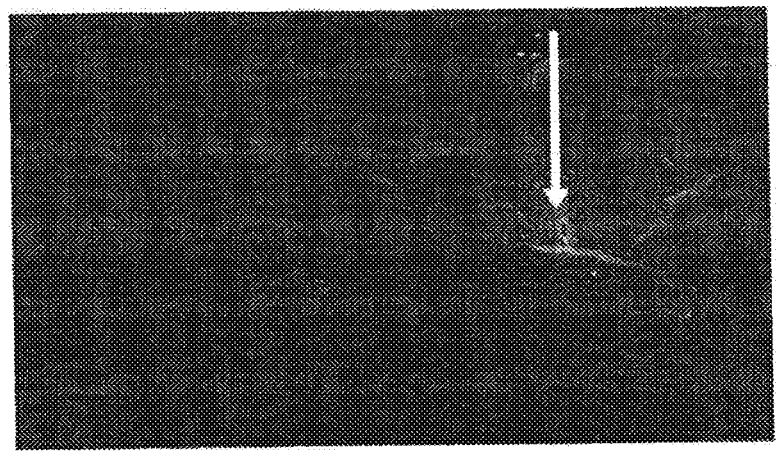
FIG. 7 shows a state in which fluorescent label $A\beta_{1-40}$ is injected in striate.

After 15 months from the start of breeding, with respect to Tg-SwDI mice (n=4) of a group administered with cilostazol-containing feed for 13.5 months and Tg-SwDI mice (n=3) of the ordinary feed administered group, Tg-SwDI mice were placed at the prone position under inhalation anesthesia using 1.5% isoflurane, midline incision of scalp was performed, and then, by using a 32 G micropipet, such that a fluorescent label $Aβ_{1-40}$ was injected for 30 seconds in the manner of stereotaxy into the striate of Tg-SwDI mice (a front part of 0.98 mm and a side part of 1.5 mm in bregma) as indicated by the arrow in FIG. 7. The depth from the brain surface to the injection site of the striate was 3.0 mm, and the fluorescent label $A\beta_{1-40}$ was purchased from AnaSpec (San Jose, Calif., USA).

After 30 minutes from the injection of the fluorescent label $A\beta_{1-40}$, the brain was taken out, and was subjected to blood removal by using a 0.01M phosphate-buffered solution. Then, a brain block instantaneously frozen by using dry ice was sliced to 20 microns with a cryostat, and serial sections are formed in the longitudinal direction of the injection site in coronal section, and a preparation was obtained. The preparation was observed with a fluorescence microscope.

Figure 8:
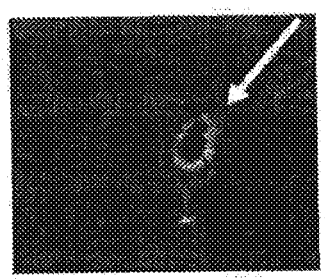
FIG. 8 shows fluorescent label in an accumulation site of a leptomeninges vessel at a distance of 2922 μm from the injection site in a Tg-SwDI mouse of the cilostazol-containing feed administered group.
Figure 9:
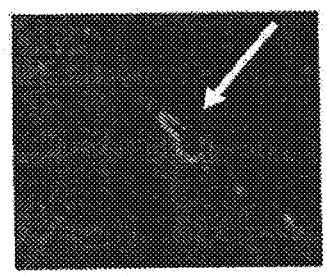
FIG. 9 shows fluorescent label $A\beta_{1-40}$ in an accumulation site of a leptomeninges vessel at a distance of 3422 μm from the injection site in a Tg-SwDI mouse of the cilostazol-containing feed administered group.
Figure 10:
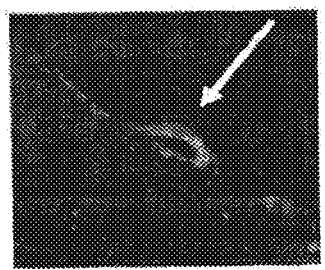
FIG. 10 shows fluorescent label $A\beta_{1-40}$ in an accumulation site of a leptomeninges vessel at a distance of 3507 μm from the injection site in a Tg-SwDI mouse of the cilostazol-containing feed administered group.

FIG. 8 shows a fluorescent label $A\beta_{1-40}$ in an accumulation site of a leptomeninges vessel located at 2922 μm from the injection site in Tg-SwDI mice of the cilostazol-containing teed administered group. FIG. 9 shows a fluorescent label $A\beta_{1-40}$ in an accumulation site of a leptomeninges vessel located at 3422 μm from the injection site in Tg-SwDI mice of the cilostazol-containing feed administered group. FIG. 10 shows a fluorescent label $A\beta_{1-40}$ in an accumulation site of a leptomeninges vessel located at 3507 μm from the injection site in Tg-SwDI mice of the cilostazol-containing feed administered group. As indicated by the arrows in FIGS. 8 to 10, in the Tg-SwDI mice of the cilostazol-containing feed administered group, Aβ that has moved from the injection site was located in perivascular space of the leptomeninges vessel. This result shows that clearance of Aβ through a drainage pathway of perivascular interstitial fluid was obtained.

Figure 11:
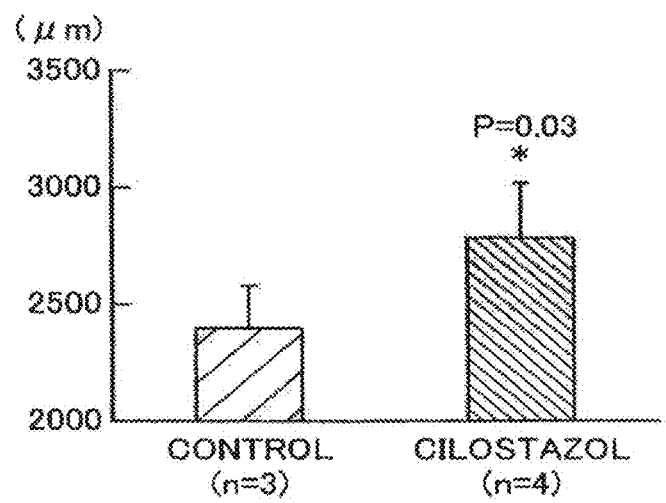
FIG. 11 is a graph showing an average travel distance of fluorescent label $A\beta_{1-40}$ from an injection site in lateral ventricle to an accumulation site of a leptomeninges vessel in Tg-SwDI mice of the cilostazol-containing feed administered group and Tg-SwDI mice of the ordinary feed administered group after 15 months from the start of breeding.
Figure 12:
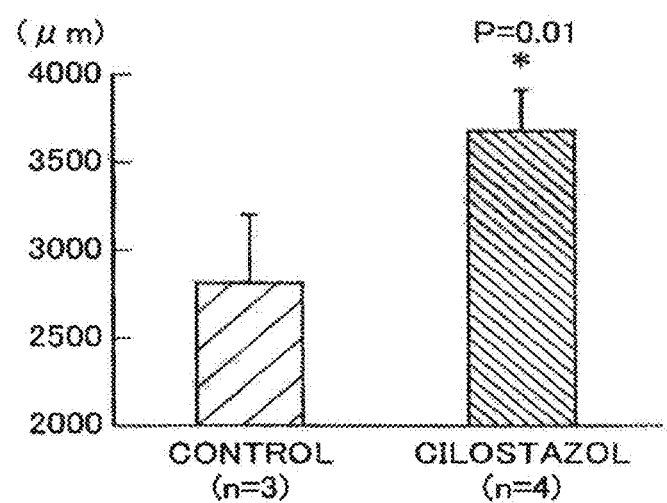
FIG. 12 is a graph showing a maximum travel distance of fluorescent label from the injection site of the lateral ventricle to the accumulation site of the leptomeninges vessel in Tg-SwDI mice of the cilostazol-containing feed administered group and the Tg-SwDI mice of the ordinary teed administered group after 15 months from the start of breeding.

FIG. 11 shows an average travel distance of the fluorescent label $A\beta_{1-40}$ from the injection site of the striate to the accumulation site of the leptomeninges vessel in Tg-SwDI mice of the group administered with cilostazol-containing feed for 13.5 months and Tg-SwDI mice of the ordinary feed administered group after 15 months from the start of breeding. FIG. 12 shows a maximum travel distance of the fluorescent label $A\beta_{1-40}$ from the injection site of the striate to the accumulation site of the leptomeninges vessel in Tg-SwDI mice of the group administered with cilostazol-containing feed for 13.5 months and Tg-SwDI mice of the ordinary feed administered group after 15 months from the start of breeding. As shown in FIGS. 11 and 12, in the Tg-SwDI mice of the cilostazol-containing feed administered group, clearance of Aβ is promoted as compared to the Tg-SwDI mice of the ordinary feed administered group. These results show that cilostazol administration facilitates drainage of harmful proteins.

(3) Inhibition of Deposition of Harmful Proteins on Cerebrovascular Lymph Drainage Pathway by Cilostazol To verify interstitial flow improvement by cilostazol, inhibition of deposition of harmful proteins on the cerebrovascular lymph drainage pathway by cilostazol was examined by using a cerebral amyloid angiopathy model. Totally unlike a drainage system through a specific receptor or antigen-antibody reaction, drainage of harmful proteins through the interstitial flow is a general drainage system irrespective of the type and amount of proteins, and Aβ in these examples is merely an example of intracerebral harmful proteins for which the interstitial flow is improved so that deposition on the cerebrovascular lymph drainage pathway is inhibited.

After 15 months from the start of breeding, with respect to Tg-SwDI mice of a group administered with cilostazol-containing feed for 13.5 months and Tg-SwDI mice of the ordinary feed administered group, the brain was perfusion-fixed by using 4% paraformaldehide, and the extracted brain was dehydrated for one day. Then, a paraffin block of a fixed brain tissue was prepared, and a paraffin block was sliced to 6 microns with a microtome. Thereafter, Aβ deposited on the vascular wall was observed with a microscope by an immunohistochemical staining for Aβ. An ImageJ (NIH) was used as image analysis software. Five regions of interest were randomly selected from the frontal lobe and the hippocampus region in a tissue section, and photographed in a field with a magnification of 200. The measured data was analyzed by using a t test.

Figure 13B:
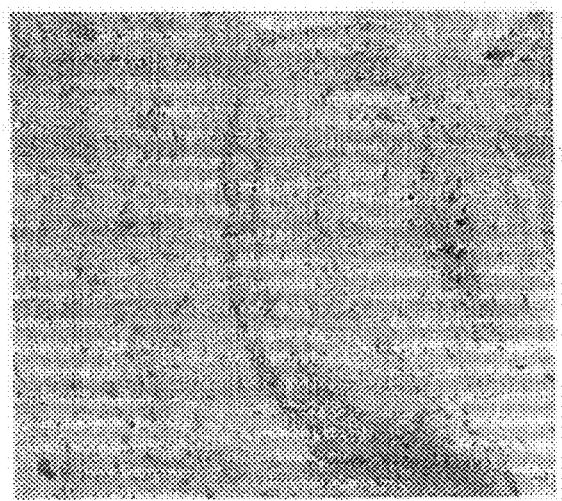
FIGS. 13A and 13B are photographs of perivascular Aβ deposition in Tg-SwDI mice of the ordinary feed administered group.
Figure 13A:
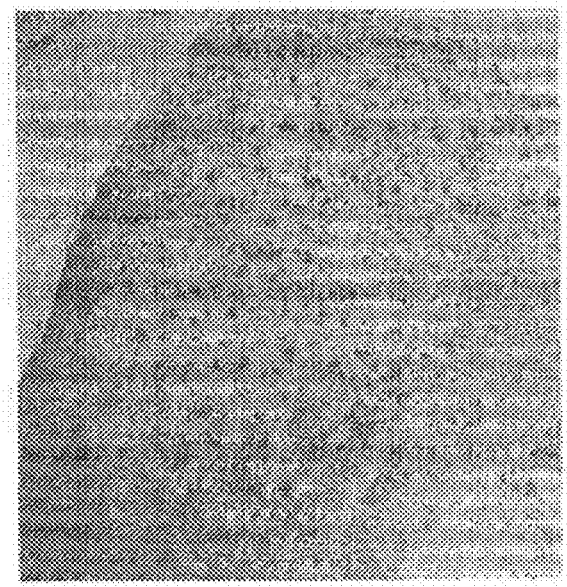
Figure 14B:
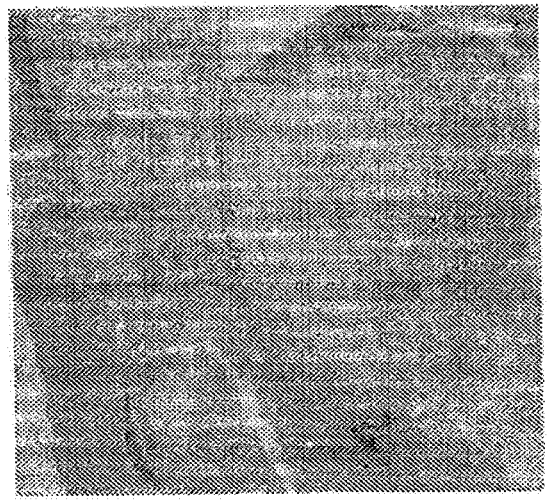
FIGS. 14A and 14B are photographs of perivascular Aβ deposition in Tg-SwDI mice of the cilostazol-containing feed administered group.
Figure 14A:
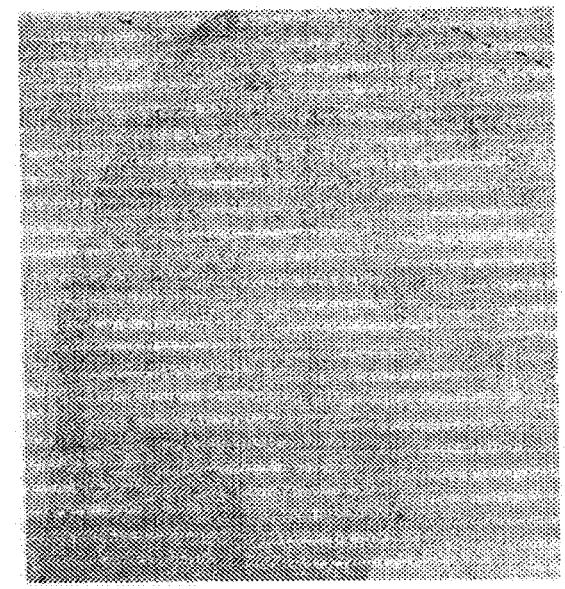

FIGS. 13A and 13B are photographs of perivascular Aβ deposition in Tg-SwDI mice of the ordinary feed administered group. FIG. 13A shows the frontal lobe, and FIG. 13B shows the hippocampus. FIGS. 14A and 14B are photographs of perivascular Aβ deposition in Tg-SwDI mice of the cilostazol-containing feed administered group. FIG. 14A shows the frontal lobe, and FIG. 14B shows the hippocampus. As indicated by the arrows in FIGS. 13A, 13B, 14A, and 14B, in either case of frontal lobe or hippocampus, the amount of Aβ deposited on a perivascular site in the Tg-SwDI mice of the cilostazol-containing feed administered group is smaller than that in the Tg-SwDI mice of the ordinary feed administered group.

Figure 15:
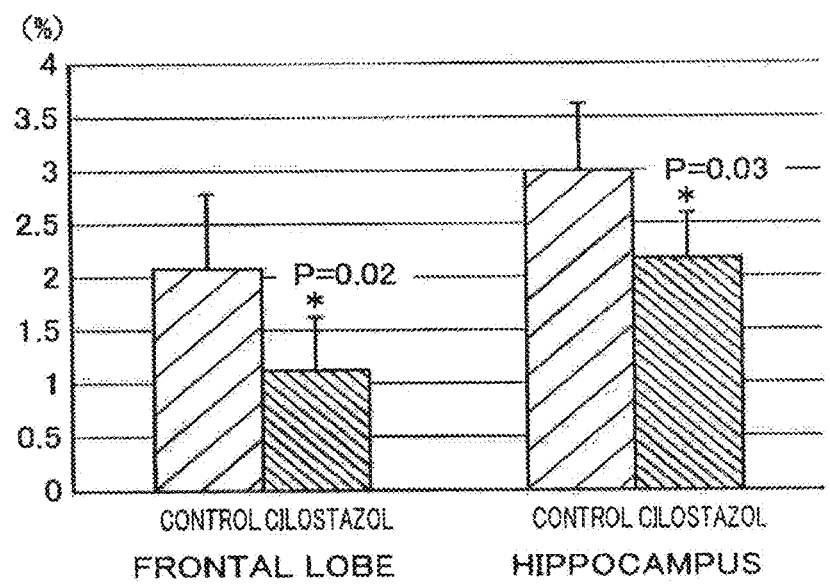
FIG. 15 is a graph showing relative decreases in Aβ in Tg-SwDI mice of a group administered with cilostazol-containing feed for 8 months and Tg-SwDI mice of the ordinary feed administered group after 12 months from the start of breeding.
Figure 16:
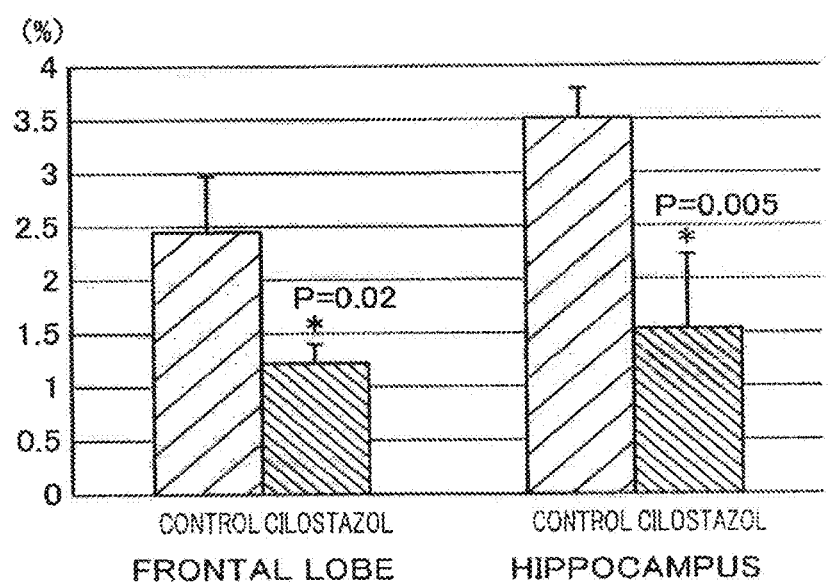
FIG. 16 is a graph showing relative decreases in AD in Tg-SwDI mice of a group administered with cilostazol-containing feed for 13.5 months and Tg-SwD1 mice of the ordinary feed administered group after 15 months from the start of breeding.

FIG. 15 shows relative decreases in Aβ in a perivascular site in Tg-SwDI mice of a group administered with cilostazol-containing feed for 8 months from 4 months of age and Tg-SwDI mice of the ordinary feed administered group after 12 months from the start of breeding. FIG. 16 shows relative decreases in Aβ in a perivascular site in Tg-SwDI mice of a group administered with cilostazol-containing feed for 13.5 months from 1.5 months of age and Tg-SwDI mice of the ordinary feed administered group after 15 months from the start of breeding. As shown in FIGS. 15 and 16, deposition of Aβ on the perivascular site in the Tg-SwDI mice of the cilostazol-containing feed administered group is reduced as compared to the Tg-SwDI mice of the ordinary feed administered group. These results show that cilostazol administration inhibits deposition of harmful proteins in the cerebrovascular site, which is a flowpath of the interstitial flow, (4) Clinical Therapeutic Effect on Elderly Persons with MMSE Score of 22 to 26, Inclusive Harmful proteins such as tau protein, α-synuclein protein, amyloid β protein, and ubiquitinated protein, which cause disorders in nerve function, are gradually accumulated in the brain with age. Irrespective of the type of accumulated harmful proteins, mild disorders in cognitive function is observed in an initial stage. However, in this stage, irreversible neuron degeneration in cranial nerve tissues has been seldom observed yet. Thus, activation of the interstitial flow, which is one of major drainage pathways of harmful proteins, might cure mild disorders of cognitive function. To examine this hypothesis, it was evaluated how consecutive oral administration of cilostazol affects cognitive functions of patients having MMSE scores greater than or equal to 22 and less than or equal to 26 and suspected to have mild deterioration of cognitive function.

A survey was conducted on consecutive cases (3183 cases in total) between 1996 and 2012 whose records of cilostazol administration exist, and examination using all the cases that match the following conditions was carried out. In this examination, to eliminate the influence of anti-dementia drugs, all the patients administered with anti-dementia drugs such as donepezil were removed from the analysis.

<Selection Conditions>

(i) The mini mental state exam (MMSE), which is a typical test of cognitive function, was performed twice or more with an interval of 6 months or more (a case where the MMSE was performed three or more times, two examination results of the first examination and the last examination were selected);

(ii) The first MMSE score was greater than or equal to 22 and less than or equal to 26;

(iii) A case in which cilostazol was administered in a period at least more than a half of an MMSE observation period was selected as a group (hereinafter referred to as a treated group) subjected to consecutive treatment; and (iv) A case in which cilostazol was administered in two months or less in the MMSE observation period was selected as a group (hereinafter referred to as an untreated group) not subjected to consecutive treatment.

<Analysis Items>

(i) The rate of change in MMSE scores in each group (calculation method: [last MMSE score−first MMSE score]/MMSE observation period [years]); and (ii) The rate of change in scores in each item of the MMSE test in each group (calculation method: [score of last MMSE test item−score of first MMSE test item]/MMSE observation period [years]).

In comparison between the two groups, statistical analysis was conducted such that the rate difference was obtained by using a chi-square test and other items were obtained by using a t test.

<Results>

Among the 3183 cases, 9 cases of the MCI untreated group and 31 cases of the MCI treated group matched the selection conditions. Background factors of the groups are: age (untreated group: 81.3±2.2 years, treated group: 76.6±1.2 years, P=0.07) [average±standard error, the same hereinafter], first MMSE score (untreated group: 23.7±0.4, treated group: 23.7±0.7, P=0.87), MMSE observation period (untreated group: 773±144 days, treated group: 645±74 days, P=0.42), and proportion of males (untreated group: 56%, treated group: 35%, P=0.28). No significant difference in patient background factor was found between the untreated group and the treated group. The untreated group is a group of patients not subjected to cilostazol consecutive treatment because of side effects such as diarrhea and headaches. Clinical manifestations of the central nervous system and the background factors were assumed to be substantially the same between the treated group and the untreated group in the first MMSE test.

Regarding the rate of change in MMSE score, the untreated group was −3.8±1.3 (per year), the treated group was 0.4±0.7 (per year). It was demonstrated that consecutive oral administration of cilostazol significantly improves the cognitive function in MCI patients (see FIG. 17, P=0.007).

Figure 18:
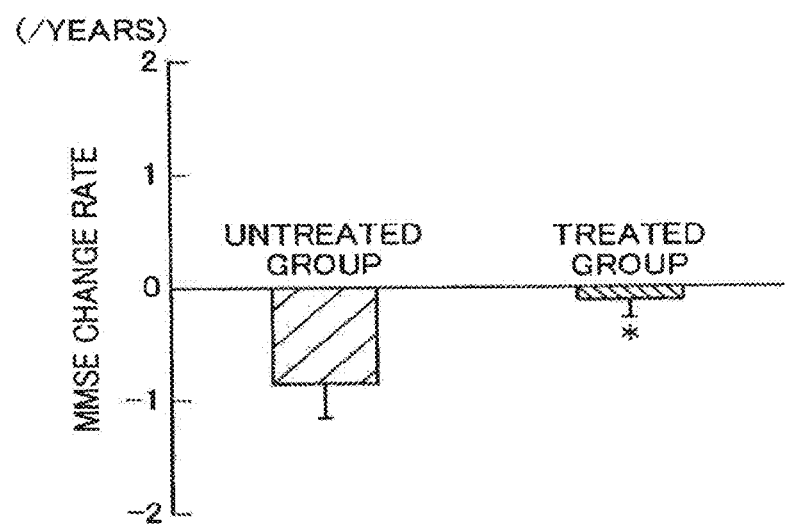
FIG. 18 is a graph showing a change ratio of orientation to time (item 1 in MMSE) of the cilostazol-administered group and the non-administered group in the MCI patient group.
Figure 19:
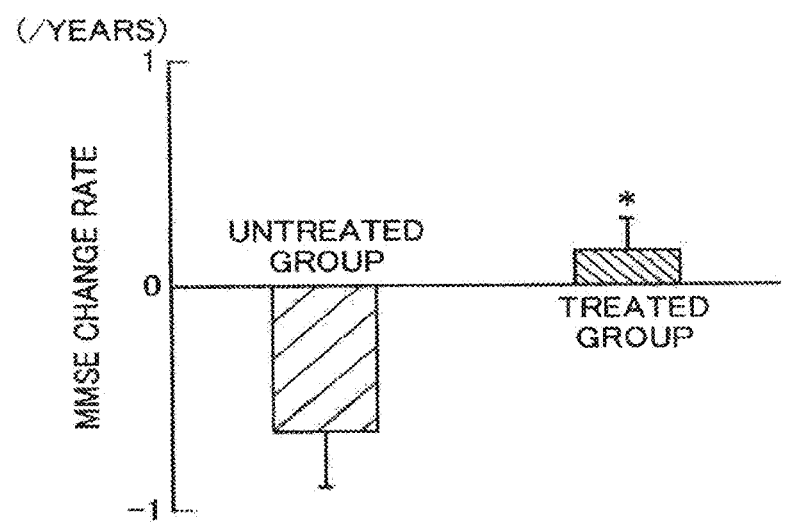
FIG. 19 is graph showing a change rate of delayed recall (item 5 in MMSE) of the cilostazol-administered group and the non-administered group in the MCI patient group.
Figure 20:
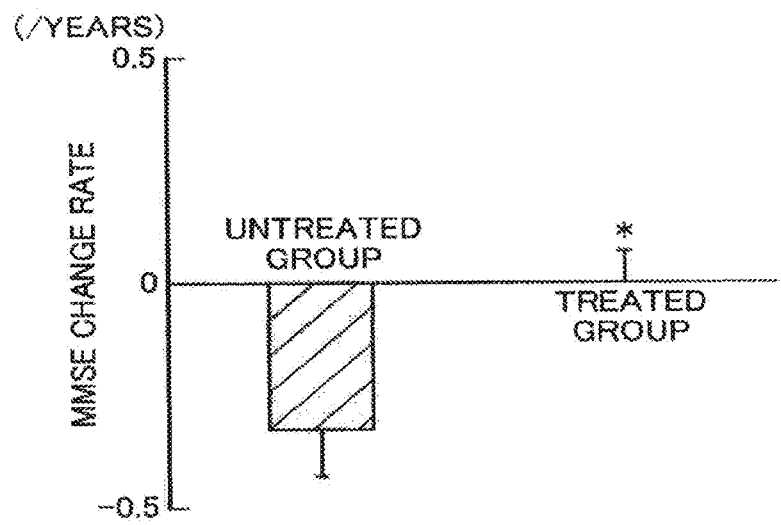
FIG. 20 is a graph showing a change rate of command with sentence (item 9 in MMSE) of the cilostazol-administered group and the non-administered group in the MCI patient group.
Figure 21:
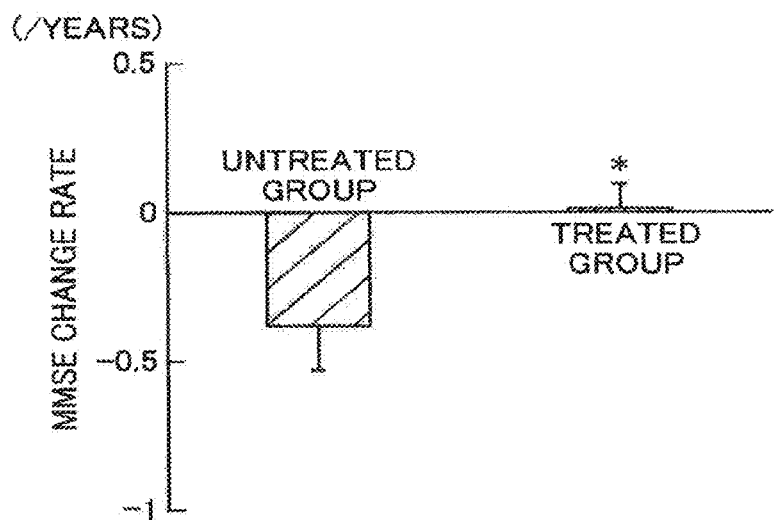
FIG. 21 is a graph showing a change rate of visual configuration (item 11 in MMSE) of the cilostazol-administered group and the non-administered group in the MCI patient group.

In addition, among the analyses for individual items regarding the rate of change in MMSE score, items showing significant differences between the two groups are four items: item 1 of orientation to time (the untreated group: −0.87±0.30, the treated group: −0.13±0.16, P=0.03, FIG. 18), item 5 of delayed recall (the untreated group: −0.66±0.24, the treated group: 0.16±0.13, P=0.004, FIG. 19), item 9 of command with sentence (the untreated group; −0.33±0.10, the treated group: 0.01±0.06, P=0.008, FIG. 20), and item 11 of visual configuration (the untreated group: −0.38±0.15, the treated group: 0.03±0.08, P=0.02, FIG. 21). Disorders of visual configuration in item 11 are known to be prone to transition to Lewy body-type dementia. In senile MCI patients, participation of intracerebral accumulation of harmful proteins such as β amyloid protein and β synuclein is suggested in most cases. The result of this example shows that the therapeutic effect of interstitial flow improvement by cilostazol is widely effective for MCI patients including a previous stage of Lewy body-type dementia. The sign "*" in the drawings indicates that P<0.05 statistically and a significant difference is present.

(5) Absence of Clinical Therapeutic Effect on Dementia Patient

There are reports of cases suggesting the possibility of an therapeutic effect of cilostazol on dementia patients ("Effect of cilostazol on dementia having vascular risk factor," Department of Neurology, Shiseikai Daini Hospital, 2011, published by a poster of the Japan Stroke Society). These reports do not use specific comparison groups, and have very low scientific utility. Thus, it is not worth referring to these reports. It is assumed that a considerable degree of irreversible neurodegeneration has progressed in dementia patients, and in view of the action mechanism of the interstitial flow-improving agent, a sufficient therapeutic effect of the interstitial flow-improving agent might not be present for dementia patients. Thus, to evaluate the influence of consecutive oral administration of cilostazol on the cognitive function, a survey of consecutive cases (3183 cases in total) for which record of cilostazol administration between 1996 and 2012 exists was conducted, and examination was conducted by using all the cases matching the following conditions. In this study, to eliminate the influence of anti-dementia drugs, patients administered with anti-dementia drugs such as donepezil were removed from the analysis.

<Selection Conditions>

(i) The mini mental state exam (MMSE), which is a typical test of cognitive function, was conducted twice or more with an interval of 6 months or more (in a case where the MMSE was performed three or more times, two examination results of the first examination and the last examination were selected);

(ii) The first MMSE score was less than or equal to 21;

(iii) A case in which cilostazol was administered in a period at least more than a half of an MMSE observation period was selected as a group (hereinafter referred to as a treated group) subjected to consecutive treatment; and (iv) A case in which cilostazol was administered in two months or less in an MMSE observation period was selected as a group (hereinafter referred to as an untreated group) not subjected to consecutive treatment.

<Analysis Items>

(i) The rate of change in MMSE score in each group (calculation method: [last MMSE score−first MMSE score]/MMSE observation period [years]). In comparison between the two groups, statistical analysis was conducted such that the rate difference was obtained by using a chi-square test and other items were obtained by using a t test.

<Results>

Among the 3183 cases, 9 dementia cases of the cilostazol untreated group and 19 cases of the treated group matched the selection conditions. Background factors of the groups are: age (untreated group: 80.7±3.2 years, treated group: 78.5±2.2 years, P=0.57) [average±standard error, the same hereinafter], first MMSE score (untreated group: 16.3±2.0, treated group: 15.0±1.3, P=0.58), MMSE observation period (untreated group: 821±125 days, treated group: 565±86 days, P=0.10), and proportion of males (untreated group: 67%, treated group: 63%, P=0.86). No significant difference in patient background factor was found between the untreated group and the treated group. The untreated group is a group of patients not subjected to cilostazol consecutive treatment because of side effects such as diarrhea and headaches. Clinical manifestations of the central nervous system and the background factors were assumed to be substantially the same between the treated group and the untreated group in the first MMSE test.

Figure 22:
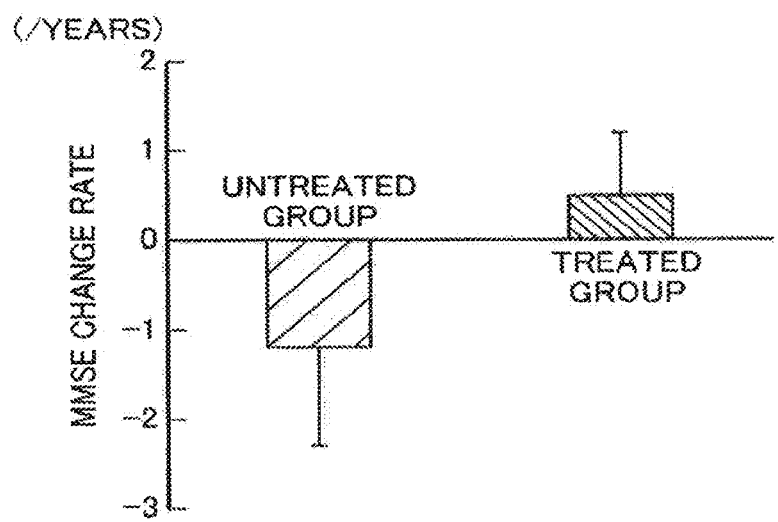
FIG. 22 is a graph showing a change rate of MMSE scores of a cilostazol-administered group and a non-administered group in a dementia patient group.

Regarding the rate of change in MMSE score, the untreated group was −1.2±1.1 (/year), the treated group was 0.5±0.7 (/year), and P value was 0.21 (see FIG. 22). An existing report shows a case where cilostazol administration might provide a therapeutic effect on dementia having a vascular risk factor ("Effect of cilostazol on dementia having vascular risk factor," Department of Neurology, Shiseikai Daini Hospital. 2011, published by a poster of the Japan Stroke Society). In this study, similarly to the cilostazol-administered group, cases showing MMSE improvement are present in cilostazol-nonadministered groups. Consequently, no statistically significant therapeutic effects on dementia were observed. In consideration of the finding of Example (4) above, a therapeutic target of cilostazol as an interstitial flow-improving agent is not dementia patients already expressing dementia but elderly persons with mild deteriorated cognitive function having an MMSE score greater than or equal to 22 and less than or equal to 26.

(6) Enhancement of Vascular Pulsation by Cilostazol Under Acetylcholine Administration In the brain interstitial flow in a central nervous system, vascular wall motion due to artery vascular pulsation serves as a driving force so that harmful proteins are excreted. Dilation of artery in vascular pulsation occurs when the blood pressure in artery increases due to pulsation of heart. A decrease in dilation ability of artery attenuates vascular wall motion, and reduces the interstitial flow accordingly. In the presence of aged mice and cerebral amyloid angiopathy, vascular elasticity (flexibility) of cerebral artery considerably decreases, and vascular wall motion attenuates. Thus, the ability of excretion of harmful proteins deteriorates. In this study, the influence of cilostazol administration on vascular elasticity ability under acetylcholine administration was examined.

It is known that acetylcholine has the physiological action of improving vascular elasticity. In a case where acetylcholine is administered to the brain surface, vascular elasticities of cilostazol-containing teed administration model mice and ordinary feed administration model mice were compared.

In a manner similar to section (1) regarding vascular elasticity enhancement by cilostazol discussed above, model mice (Tg-SwDI mice) (Davis et al, 2004) showing pathological changes, especially cerebral amyloid angiopathy, were used. In the examination, 16 male Tg-SwDI mice aged 4 months were prepared and classified into two groups: a cilostazol-containing feed administered group (n=9) and an ordinary feed administered group (n=7). These mice were grown to the age of 12 months. The cilostazol concentration in cilostazol-containing feed was 0.3 wt %. In the 16 Tg-SwD1 mice, a cranial window with a diameter of 2 mm was generated, and then, dura mater was removed and a Ringer solution was perfused. Thereafter, acetylcholine (100 µM) was perfused at a flow rate of 100 µL/min. Cerebral blood vessels were visualized with FITC-dextran, and the rate of change in vessel diameter from a time before administration to 3 minutes after the start of administration was analyzed.

After 12 months from the start of breeding, with respect to Tg-SwDI mice of the cilostazol-containing feed administered group and Tg-SwDI mice of the ordinary feed administered group, Tg-SwDI mice were placed under inhalation anesthesia using 1.5% isoflurane, and relative increases in cerebrovascular diameter of the Tg-SwDI mice of the cilostazol-containing feed administered group and the Tg-SwDI mice of the ordinary feed administered group were evaluated. The cerebrovascular diameters were measured in an cranial window formed (2 mm×2 mm), and FITC-dextran was injected through tail veins so that blood vessels were visualized.

Figure 23:
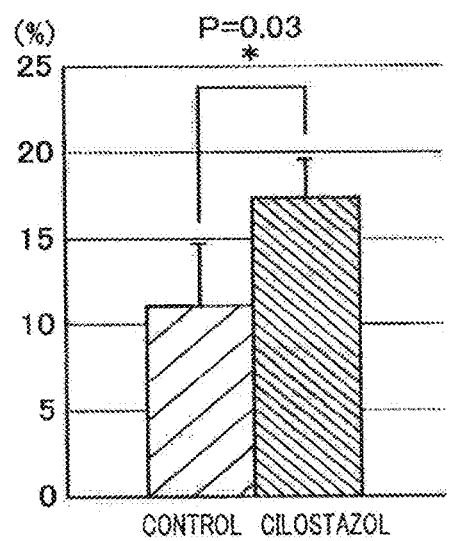
FIG. 23 is a graph showing relative increases in cerebrovascular diameter in Tg-SwDI mice of a group administered with cilostazol-containing feed for 8 months and Tg-SwDI mice of the ordinary feed administered group under acetylcholine administration.

FIG. 23 shows relative increases in cerebrovascular diameter in Tg-SwDI mice of a group administered with cilostazol-containing feed for 8 months and Tg-SwDI mice of the ordinary feed administered group after 12 months of age.

Figure 24:
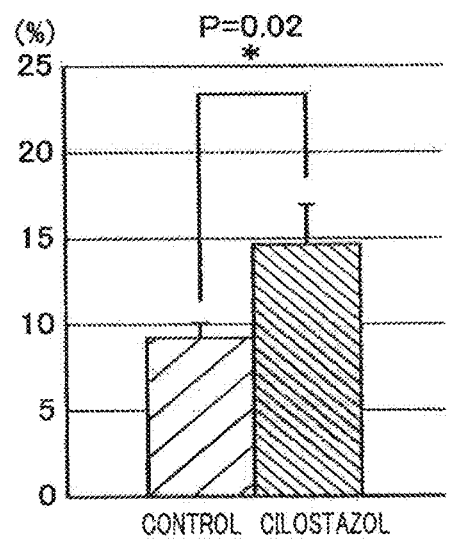
FIG. 24 is a graph showing relative increases in cerebrovascular diameter in Tg-SwDI mice administered with cilostazol-containing feed for 13.5 months and Tg-SwDI mice of the ordinary feed administered group under acetylcholine administration.

Then, 16 male Tg-SwDI mice aged 1.5 months were prepared and classified into two groups: a cilostazol-containing feed administered group (n=9) and an ordinary feed administered group (n=7). These mice were grown to the age of 15 months. The other conditions are the same as those described above, and vascular elasticity was tested. FIG. 24 shows relative increases in cerebrovascular diameter in Tg-SwDI mice administered with cilostazol-containing feed for 13.5 months and Tg-SwDI mice of the ordinary feed administered group after 15 months of age.

As shown in FIGS. 23 and 24, in the case of administration of acetylcholine to the brain surface, blood vessels of the Tg-SwDI mice of the cilostazol-containing feed administered group are dilated as compared to the Tg-SwDI mice of the ordinary feed administered group. It is suggested that combined administration of cilostazol and acetylcholine markedly increases vascular elasticity, as compared to the case of single administration of acetylcholine.

Figure 25:
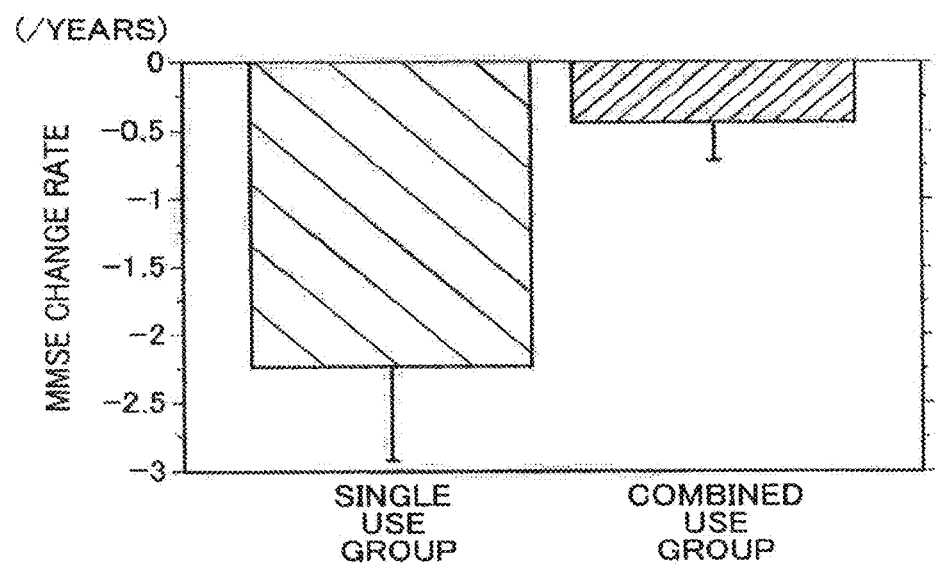
FIG. 25 is a graph showing a change rate of MMSE scores in a donepezil hydrochloride administered group and a cilostazol- and donepezil hydrochloride-combined use group in an MCI patient group with MMSE scores greater than or equal to 22 and less than or equal to 26.
Figure 26:
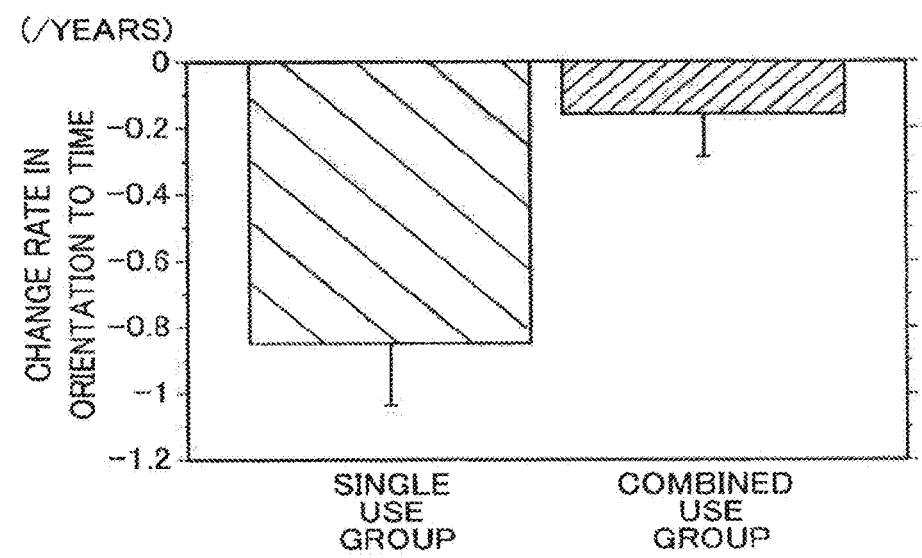
FIG. 26 is a graph showing a change rate of orientation to time (item 1 in MMSE) in the donepezil hydrochloride administered group and the cilostazol- and donepezil hydrochloride-combined use group in the MCI patient group with MMSE scores greater than or equal to 22 and less than or equal to 26.
Figure 27:
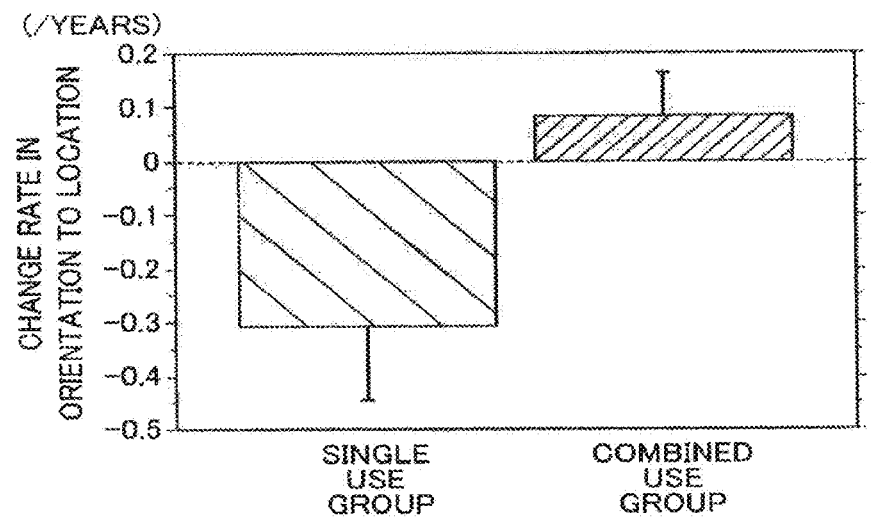
FIG. 27 is a graph showing a change rate of orientation to location (item 2 in MMSE) in the donepezil hydrochloride administered group and the cilostazol- and donepezil hydrochloride-combined use group in the MCI patient group with MMSE scores greater than or equal to 22 and less than or equal to 26.
Figure 28:
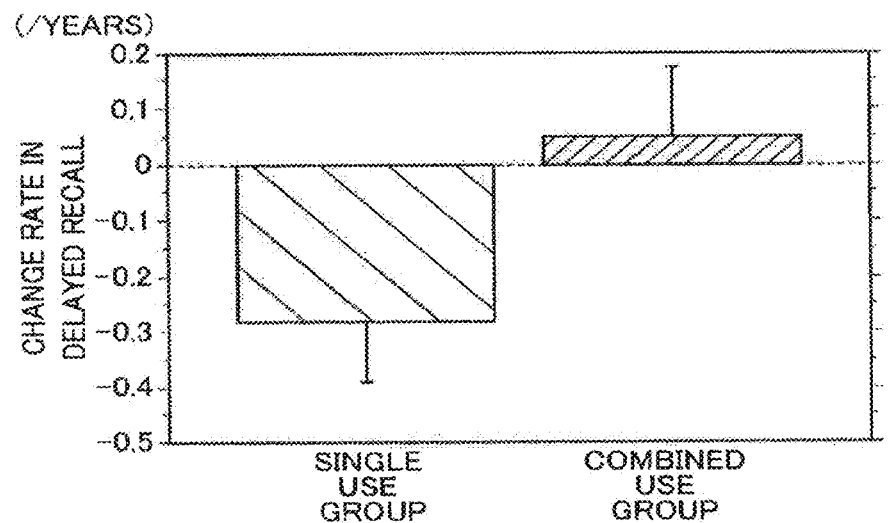
FIG. 28 is a graph showing a change rate of delayed recall (item 5 in MMSE) of the donepezil hydrochloride administered group and the cilostazol- and donepezil hydrochloride-combined use group in the MCI patient group with MMSE scores greater than or equal to 22 and less than or equal to 26.

(7) Clinical Therapeutic Effect on Elderly Persons Subjected to Oral Administration of Donepezil Hydrochloride and Having MMSE Scores of 22 to 26, Inclusive Patients subjected to oral administration of donepezil hydrochloride, having an observation period of one or more years before the MMSE test date, and having first MMSE scores less than or equal to 26 were picked up from a clinical record. Among the patients, patients recorded to have been consecutively administered with cilostazol for 6 months or more in the observation period were classified as a donepezil hydrochloride and cilostazol combined use group (69 cases), and patients recorded to have experienced no cilostazol oral administration were classified as a donepezil hydrochloride single use group (87 cases). Cilostazol was oral-administered at a dosage of 50 to 200 mg/day in the morning and evening, and donepezil hydrochloride was administered at a dosage of 5 mg/day once in a day. Among the patients, patients with MMSE scores greater than or equal to 22 and less than or equal to 26 were extracted as an MCI patient group. Then, 36 cases (16 males and 20 females, average age: 78.4 years old) of the donepezil hydrochloride single use group (hereinafter referred to as a single use group) and 34 cases (15 males and 19 females, average age: 77.2 years old) of the donepezil hydrochloride and cilostazol combined use group (hereinafter referred to as combined use group) were found. The average dosage of cilostazol in the combined use group was 121 mg/day. In the first MMSE in the observation period, the score of the single use group was 24.0±1.3 (average±standard error) and the score of the combined use group was 24.2±1.5. No significant difference was observed between the two groups (p=0.43): The observation period was 30.4±2.1 months for the single use group, and 28.6±2.0 months for the combined use group. No significant difference was observed between (p=0.52): The 36 cases of the single use group and the 34 cases of the combined use group were analyzed, and the rate of change in MMSE score in the observation period (increment or decrement value of MMSE score in each patient/MMSE observation period [year]) was examined. Measurement of MMSE was conducted at least twice in the observation period, and the first and last test results were selected for analysis. The MMSE change rates were −2.23±0.69 in the single use group, and −0.45±0.28 in the combined use group. A significant difference was observed between the two groups (p=0.022) (see FIG. 25). This result shows that in MCI patients under donepezil hydrochloride oral administration, additional oral administration of cilostazol reduced the annual decrease rate of MMSE scores by about 80%. In addition, in analysis of each MMSE subitem, significant differences in the change rate (increment or decrement value in each item/MMSE observation period [year]) between the two groups were found in the following three items: item 1 of orientation to time (single use group: −0.85 vs. combined use group: −0.16, p=0.003) (FIG. 26), item 2 of orientation to location (single use group: −0.31 vs. combined use group: +0.09, p=0.017) (FIG. 27), and item 5 of delayed recall (single use group: −0.28 vs. combined use group: +0.05; p=0.045) (FIG. 28). In the first MMSE test, regarding item 1 (single use group: 3.9±0.2 vs. combined use group: 4.1±0.2, p=0.74), item 2 (single use group: 4.4±0.1 vs. combined use group: 4.3±0.17, p=0.1), and item 5 (single use group: 2.1±0.2 vs. combined use group: 1.9±0.2, p=0.28), no significant differences were observed between the two groups, and it is shown that cilostazol can prevent deterioration of orientations and delayed recall. For the foregoing reasons, on the analogy of the results on model animals shown in section (7) above, the combined use of cilostazol and donepezil hydrochloride is clinically proved to be effective for MCI.

(8) Absence of Clinical Therapeutic Effect on Dementia Patient Oral-Administered with Donepezil Hydrochloride There is a report (Japanese Unexamined Patent Publication (Japanese Translation of PCT Application) No. 2010-527993, Otsuka Pharmaceutical Co., Ltd.) on a case suggesting a therapeutic effect of cilostazol in dementia patients oral-administered with donepezil hydrochloride. However, this report does not use a comparison group, and has very low scientific utility. Thus, it is not worth referring to this report.

Figure 29:
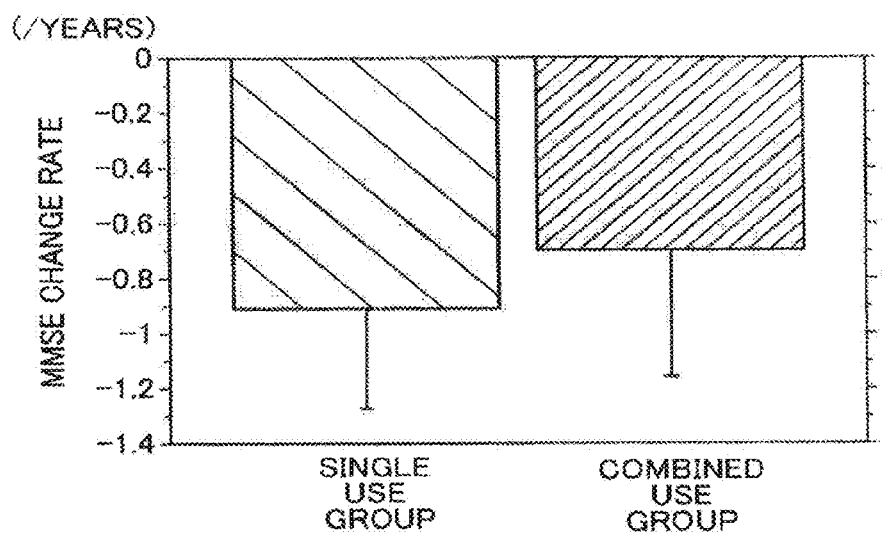
FIG. 29 is a graph showing a change rate of MMSE scores of a donepezil hydrochloride administered group and a cilostazol- and donepezil hydrochloride-combined use group in an MCI patient group with MMSE scores less than or equal to 21.
Figure 30:
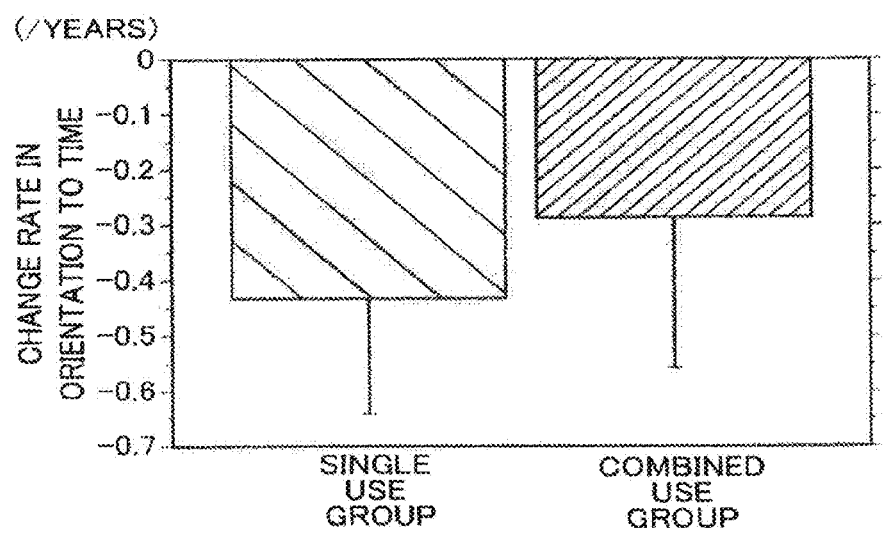
FIG. 30 is a graph showing a change rate of orientation to time (item 1 in MMSE) of the donepezil hydrochloride administered group and the cilostazol- and donepezil hydrochloride-combined use group in the MCI patient group with MMSE scores less than or equal to 21.
Figure 31:
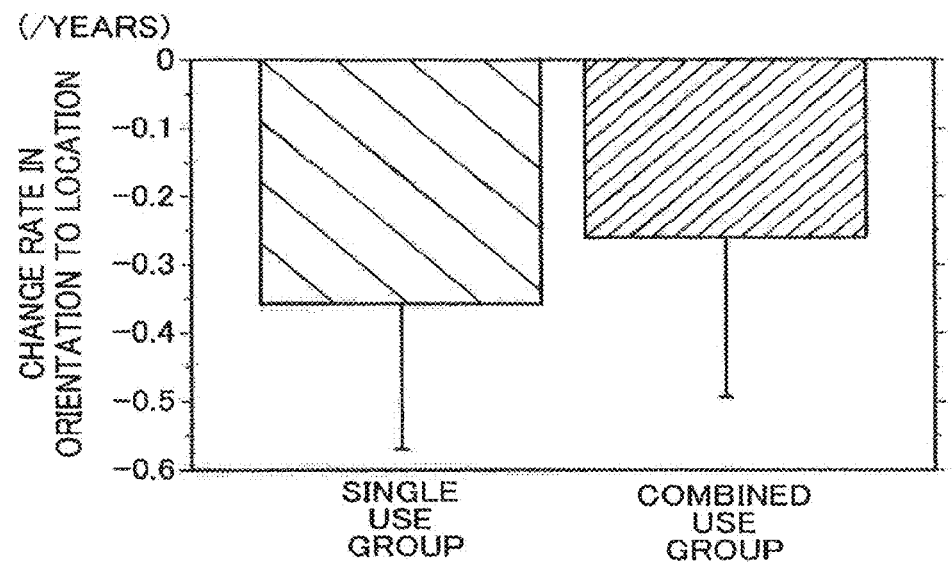
FIG. 31 is a graph showing a change rate of orientation to location (item 2 in MMSE) of the donepezil hydrochloride administered group and the cilostazol- and donepezil hydrochloride-combined use group in the MCI patient group with MMSE scores less than or equal to 21.
Figure 32:
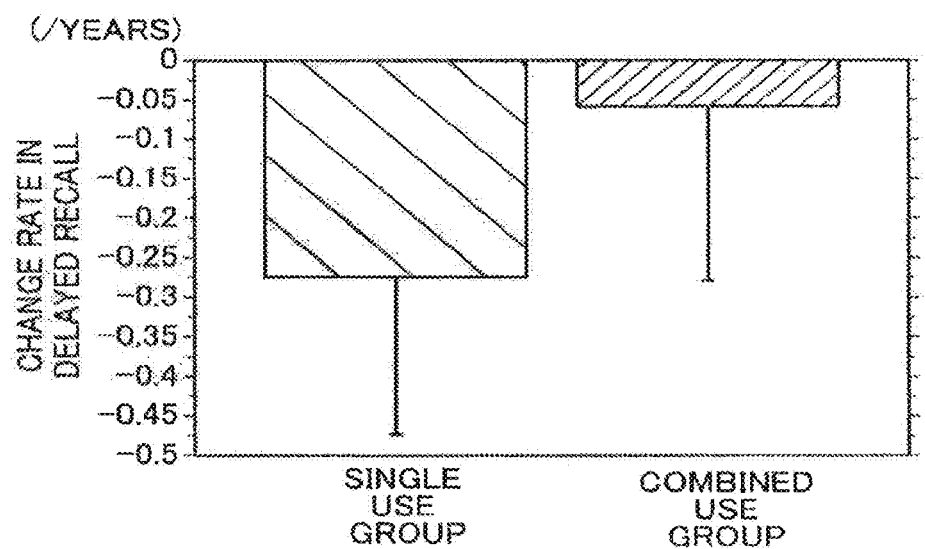
FIG. 32 is a graph showing a change rate of delayed recall (item 5 in MMSE) of the donepezil hydrochloride administered group and the cilostazol- and donepezil hydrochloride-combined use group in the MCI patient group with MMSE scores less than or equal to 21.

As a dementia patient group oral-administered with donepezil hydrochloride, patients with MMSE scores less than or equal to 21 were extracted. Then, the donepezil hydrochloride single use group (the single use group) was 51 cases (17 males and 34 females, average age: 78.2 years old) and the donepezil hydrochloride and cilostazol combined use group (the combined use group) was 35 cases (14 males and 21 females, average age: 79.3 years old). The average dosage of cilostazol in the combined use group was 139 mg/day. The first MMSE scores in the observation period were 16.5±0.68 (average±standard error) in the single use group and 15.9±0.72 in the combined use group. No difference was observed between the two groups (p=0.51). The observation period was 30.2±1.7 months in the single use group, and 25.8±1.7 months in the combined use group. No significant difference was observed (p=0.08). The 51 cases of the single use group and the 35 cases of the combined use group were analyzed, and the rates of change in MMSE score in the observation period (increment or decrement value MMSE score in each patient/MMSE observation period wears) were examined. Measurement of MMSE was conducted at least twice in the observation period, and the first and last test results were selected for analysis. The MMSE change rates were −0.90±037 in the single use group, and −0.69±0.47 in the combined use group. No significant difference was observed between the two groups (p=0.72) (see FIG. 29). Regarding subitems of MMSE including item 1 of orientation to time (single use group: −0.16 vs. combined use group: −0.13, p=0.89) (FIG. 30), item 2 of orientation to location (single use group: −0.13 vs, combined use group: +0.09, p=0.86) (FIG. 31), and item 5 of delayed recall (single use group: −0.15 vs. combined use group: −0.02, p=0.37) (FIG. 32), no significant difference was observed in any item. For the foregoing reasons, no effectiveness for dementia in cilostazol was shown. In combination with the finding of "(7) Clinical Therapeutic Effect on MCI Patient Oral-administered with Donepezil Hydrochloride," the inventors of the present invention found that in the donepezilhydrochloric acid combined use group, a therapeutic target of cilostazol as an interstitial flow-improving agent is not dementia patients already suffering from dementia but elderly persons showing mild deterioration of cognitive function, i.e., having MMSE scores greater than or equal to 22 and less than or equal to 26.

INDUSTRIAL APPLICABILITY

The present invention is useful for treatment of diseases, including MCI, caused by accumulation of harmful proteins in intracerebral sites.

The invention claimed is:

1. A method for improving interstitial flow, the method comprising:
   administering an effective amount of an agent comprising cilostazol to a patient.

2. The method of claim 1, the method comprising:
   improving interstitial flow flowing in cerebral blood vessel wall.

3. The method of claim 1, wherein the patient is a mild cognitive impairment patient.

4. The method of claim 1, wherein the patient has mini-metal state examination scores from 22 to 26.

* * * * *